United States Patent
Paczkowski et al.

(10) Patent No.: US 10,647,809 B2
(45) Date of Patent: May 12, 2020

(54) VISCOSITY MODIFICATION OF ORGANIC PHASE CONTAINING COMPOSITIONS

(71) Applicant: Lubrizol Advanced Materials, Inc., Cleveland, OH (US)

(72) Inventors: Mark A. Paczkowski, Broadview Hts., OH (US); Mallory L. McMahon, Lakewood, OH (US); Anchuu Wu, Broadview Hts., OH (US); Mana Tamami, North Royalton, OH (US); Jay W. Johnson, II, Copley, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 15/532,880

(22) PCT Filed: Dec. 3, 2015

(86) PCT No.: PCT/US2015/063604
§ 371 (c)(1),
(2) Date: Jun. 2, 2017

(87) PCT Pub. No.: WO2016/090081
PCT Pub. Date: Jun. 9, 2016

(65) Prior Publication Data
US 2017/0327623 A1    Nov. 16, 2017

Related U.S. Application Data

(60) Provisional application No. 62/087,332, filed on Dec. 4, 2014.

(51) Int. Cl.

| | |
|---|---|
| *A61K 8/31* | (2006.01) |
| *A61K 8/84* | (2006.01) |
| *A61K 8/87* | (2006.01) |
| *A61K 8/92* | (2006.01) |
| *C08G 18/10* | (2006.01) |
| *C08G 18/22* | (2006.01) |
| *C08G 18/28* | (2006.01) |
| *C08G 18/32* | (2006.01) |
| *C08G 18/42* | (2006.01) |
| *C08G 18/62* | (2006.01) |
| *C08G 18/66* | (2006.01) |
| *C08G 18/73* | (2006.01) |
| *C08L 75/02* | (2006.01) |
| *C08L 75/04* | (2006.01) |

(52) U.S. Cl.
CPC ........... *C08G 18/6208* (2013.01); *A61K 8/31* (2013.01); *A61K 8/84* (2013.01); *A61K 8/87* (2013.01); *A61K 8/922* (2013.01); *C08G 18/10* (2013.01); *C08G 18/227* (2013.01); *C08G 18/2825* (2013.01); *C08G 18/2865* (2013.01); *C08G 18/3206* (2013.01); *C08G 18/4277* (2013.01); *C08G 18/6607* (2013.01); *C08G 18/73* (2013.01); *C08L 75/02* (2013.01); *C08L 75/04* (2013.01)

(58) Field of Classification Search
CPC .......... C08G 18/6208; C08G 18/6607; C08G 18/73; C08G 18/10; C08G 18/227; C08G 18/2825; C08G 18/3206; C08G 18/2865; C08G 18/4277; A61K 8/87; A61K 8/31; A61K 8/84; A61K 8/922; C08L 75/02; C08L 75/04
See application file for complete search history.

(56) References Cited

U.S. PATENT DOCUMENTS

| | | | |
|---|---|---|---|
| 5,554,586 A | 9/1996 | Pratt | |
| 2002/0076425 A1 | 6/2002 | Mondet et al. | |
| 2003/0113285 A1* | 6/2003 | Meffert | A61K 8/87 424/70.12 |
| 2010/0190648 A1* | 7/2010 | Tollington | A01N 25/04 504/234 |

FOREIGN PATENT DOCUMENTS

WO    2007135384 A2    11/2007

OTHER PUBLICATIONS

Cuney et al., "Hydroxyl-Terminated Oligomers Crosslinked by Alkoxysilane Sol-Gel or Polyurethane Chemistries: A Comparison", Journal of Applied Polymer Science, vol. 65, 1997, pp. 2373-2386.*
R. Gallego et al., "Isocyanate-Functionalized Chitin and Chitosan as Gelling Agents of Castor Oil", Molecules, Jun. 3, 2013, pp. 6532-6549, vol. 18.

* cited by examiner

*Primary Examiner* — Patrick D Niland
(74) *Attorney, Agent, or Firm* — Christopher P. Demas; Teresan W. Gilbert

(57) ABSTRACT

The disclosed technology relates to structurant polymers based on polyurethane/polyurea chemistry, which efficiently thicken or gel (i.e., provide structure to) oils and oil mixtures. The disclosed technology further relates to structurant polymers based on polyurethane/polyurea chemistry that are oil soluble or oil dispersible and that provide beneficial properties, such as, for example, desirable clarity and/or feel. In addition, the technology relates to cosmetically and/or household acceptable formulations containing an oil as well as a structurant polymer based on polyurethane/polyurea chemistry.

11 Claims, No Drawings

VISCOSITY MODIFICATION OF ORGANIC PHASE CONTAINING COMPOSITIONS

BACKGROUND OF THE INVENTION

The disclosed technology relates to structurant polymers based on polyurethane/polyurea chemistry, which efficiently thicken or gel (i.e., provide structure to) oils and oil mixtures. The disclosed technology further relates to structurant polymers based on polyurethane/polyurea chemistry that are oil soluble or oil dispersible and that provide beneficial properties, such as, for example, desirable clarity and/or feel. In addition, the technology relates to cosmetically and/or household acceptable formulations containing an oil as well as a structurant polymer based on polyurethane/polyurea chemistry.

In the personal care industry, organic phase materials, i.e., oils, emollients, fragrances etc., are used in lotions, crémes and other products to replenish the oils lost from a substrate, such as skin or hair, during cleansing in order to keep the substrate hydrated, and to improve visual appearance and sensory perception. Most oils and emollients used in the personal care industry are low viscosity fluids which, if used alone, are difficult to handle due to their low viscosity and low surface tension. In addition, various combinations of oils and emollients are often used to provide a pleasant sensory experience that would be otherwise difficult to obtain from single or simple mixture of oils/emollients due to the heavy or tacky feeling of many of the oils and emollients.

A good deal of effort has been dedicated to the development of thickeners and sensory modifiers for such oil systems but there are large gaps in the current technologies. For example, with respect to thickening of oils, US 2010/0190648, published Jul. 29, 2010 to Croda International, teaches a structured oil system of an oil and a structurant oligomer including urethane and/or urea linkages. The structurant oligomer is limited to those derived from dimer or trimer fatty acids.

However, oils and emollients, and even fragrances used in the personal care industry span the range of polarities. Current oil thickeners on the market work very well with low polarity oils such as isohexadecane and mineral oil or with very polar oils and solvents, but there are fewer that work with medium polar oils and emollients or span a large range of oil polarities. In addition, it is much more difficult finding thickener systems that work across oil types and mixtures and leave a highly clear system. The availability of one thickener system would not address the varying oil types.

In addition, characterization of the polarity of oils, emollients and fragrances is a difficult process since many of those used are not a single molecule but, especially in natural oils, are mixtures of molecules with various but similar structures, which may contain polar groups not found in the main chemical species. Depending on the thickening mechanism, these lower concentration species can have a pronounced effect on the thickening ability of a thickener.

There are several different mechanisms by which liquids can be thickened: these include hydrodynamic volume, microgels, fibrils and associative molecules or combinations of these. The challenge in commercial formulations is to find materials that will thicken or gel the liquid in the most efficient and lowest cost manner. In all cases, the material used to thicken or gel the oil should be easily soluble or dispersible in the oil. Since oils possess a wide range of polarities, it is difficult to find a single system that will work for all oils. Furthermore, the rheological response that one needs or wants must be factored in the selection of the mechanism since interactions can lead to unpleasant results. Current commercial oil thickeners and gellants use a variety of chemistries which result in a complex understanding of where certain technologies can and cannot be used.

Accordingly, there is a need for new solutions to the problem of thickening formulations containing an organic phase.

SUMMARY OF THE INVENTION

The disclosed technology provides structurant polymers based on polyurethane/polyurea chemistry to thicken or gel an organic phase and mixtures of organic phase materials, such as oils and oil mixtures. The disclosed technology further provides structurant polymers based on polyurethane/polyurea chemistry that are soluble or dispersible in an organic phase and that provide beneficial properties, such as, for example, desirable clarity and/or feel. In addition, the technology provides cosmetically and/or household acceptable formulations containing an organic phase and a structurant polymer based on polyurethane/polyurea chemistry.

In an embodiment, the technology includes an organic phase composition. The organic phase composition can include A) from about 0.01 to about 10 wt. % of a structurant polymer, and B) at least one organic phase. In an embodiment, the organic phase can be present as a majority of the composition. As used herein, "majority" means more than 50 wt %, or more than 60 wt %, or even 70 or 80 wt %, and in an embodiment, from about 50 to 99.5 wt %.

One aspect of the present technology includes a structurant polymer. The structurant polymer can include i) hard segments, and ii) soft segments. The hard segments of the structurant polymer can be derived from 1) at least one linear non-branched aliphatic diisocyanate, or 2) at least one linear non-branched aliphatic diisocyanate in combination with at least one chain extending compound. The soft segment of the structurant polymer can have an average molecular weight of between about 500 and 6000 and can be derived from at least one hydrophobic oligomer. In one embodiment, the average molecular weight between respective diisocyanates on the structurant polymer backbone can be from between about 500 to about 2000.

In an embodiment, at least one hydrophobic oligomer can be at least one polyol compound, polyamine compound, or mixtures thereof. In a particular embodiment, the hydrophobic oligomer can be chosen from at least one of a hydrogenated polybutadiene (HPBD), polytetrahydrofuran (pTHF), polypropylene glycol (PPG), polyester, polycaprolactone, polycarbonate, polycastor oil, fatty acid/alcohol adduct, or mixtures thereof. In further embodiments, the hydrophobic oligomer can be in the form of an adduct with a lactone, diacid, or mixture thereof. In embodiments, the hydrophobic oligomer can be modified with an alcohol, amine, anhydride, or mixture thereof. In one embodiment, the hydrophobic oligomer is modified with no more than 2 mole % of a diamine.

In an embodiment, the structurant polymer can be a polyurethane. In another embodiment, the structurant polymer can be a polyurea. In a further embodiment, the structurant polymer can be a mixed polyurethane/polyurea.

In an aspect of the organic phase compositions of the present technology there can be employed an organic phase. In an embodiment, the organic phase can be derived from an animal oil, vegetable oil, mineral oil, synthetic oil, or mixture thereof. In a further embodiment, the organic phase can be hydrogenated.

In an embodiment of the organic phase compositions of the present technology, the ratio of the total hydrogen bonding donor sites to the total hydrogen bonding acceptor sites in the organic phase composition can be about 1 or greater. In a further embodiment, the ΔHSP (defined below) between the oil and the polymer can be less than about 4.

The present technology also include a method of thickening an organic phase composition. In an embodiment, the method include adding to an organic phase up to about 10 wt. % of a structurant polymer as herein described.

DETAILED DESCRIPTION OF THE INVENTION

Various preferred features and embodiments will be described below by way of non-limiting illustration.

Without limitation, the present technology includes a structurant polymer, as well as a composition containing the structurant polymer in an organic phase. The structurant polymer provides at least one of thickening/gelling or clarity to the organic phase composition, as well as improved sensorial properties.

Structurant Polymer

The structurant polymer can be a polyurethane, polyurea, or a mixed polyurethane/polyurea polymer.

As a polyurethane, the structurant polymer can have a number average molecular weight ("Mn") of from about 7,000 to about 40,000, or from about 8,000 to about 32,000, or from about 9,000 to about 25,000. In some embodiments, the structurant polymer can have an Mn of about 8,000 or 10,000 to about 20,000 or 30,000.

As a polyurea, or mixed polyurethane/polyurea, the structurant polymer can have a number average molecular weight ("Mn") of from about 7,000 to about 40,000, or from about 8,000 to about 32,000, or from about 9,000 to about 25,000. In some embodiments, the structurant polymer can have an Mn of about 8,000 or 10,000 to about 30,000.

The structurant polymer can contain (i) hard segments, including diisocyanates and chain extenders, and (ii) soft segments of hydrophobic oligomers.

The Soft Segments

The soft segments of the structurant polymer can be derived from at least one hydrophobic oligomer (that is, a single hydrophobic oligomers or mixture of two or more different hydrophobic oligomers). The average molecular weight of the at least one hydrophobic oligomer employed in the structurant polymer, and thus, the soft segments of the structurant polymer can be less than about 6,000, such as, for example, less than 5,000, or less than 3,000, or less than about 2,500, or even less than about 2,000. In some embodiments, the average molecular weight of the hydrophobic oligomers and thus, the soft segments in the structurant polymer can be between about 250 or 500 and about 6,000, or 3,000, or between about 750 and about 4,500, or from about 500 to about 3,000. In further embodiments, the molecular weight of the hydrophobic oligomers and thus, the soft segments can be, on average, less than about 2,000, or less than about 1,500, or even less than about 1,250 or 1,000. In some embodiments, the average molecular weight of the hydrophobic oligomers and thus, the soft segments in the structurant polymer can be between about 500 and about 2,000, or between about 500 and about 1,500, or between about 750 and about 1,250, or from about 250 to about 1,000. By average molecular weight, it is meant the sum of the molecular weights of the hydrophobic oligomers/soft segments divided by the total number of hydrophobic oligomers/soft segments.

The hydrophobic oligomers in the soft segment of the structurant polymer can be polyols, polyamines, or mixtures thereof.

An example polyol hydrophobic oligomer used in synthesizing the polymer can be, for example, a diol of a conjugated diolefin monomer; polyether polyols; polyesters; polycaprolactones; polycarbonates; polycastor oils; fatty acid/alcohols adducts, or mixtures thereof.

Diols of conjugated olefin monomers that can be used can include hydrogenated polybutadienediols, and hydrogenated polyisoprene diol. Hydrogenated polybutadiene ("HPBD") polyols are sold by Nippon Soda Co., Ltd under the trade name Nisso-PB™ and Krasol™ polyols sold by Cray Valley USA, LLC. In an embodiment, the hydrophobic oligomer is a hydrogenated polybutadiene.

Suitable polyether polyols include polyether polyols derived from a diol or polyol having a total of from 2 to 15 carbon atoms, in some embodiments an alkyl diol or glycol which is reacted with an ether comprising an alkylene oxide having from 2 to 6 carbon atoms, typically ethylene oxide or propylene oxide or mixtures thereof. For example, hydroxy functional polyether can be produced by first reacting propylene glycol with propylene oxide followed by subsequent reaction with ethylene oxide. Primary hydroxy groups resulting from ethylene oxide are more reactive than secondary hydroxy groups and thus are preferred. Useful commercial polyether polyols include poly(ethylene glycol) comprising ethylene oxide reacted with ethylene glycol, polypropylene glycol) comprising propylene oxide reacted with propylene glycol, poly(tetramethylene ether glycol) comprising water reacted with tetrahydrofuran which can also be described as polymerized tetrahydrofuran or pTHF, and which is commonly referred to as PTMEG. In some embodiments, the polyether intermediate includes PTMEG. Copolyethers can also be utilized in the described compositions. Typical copolyethers include the reaction product of THF and ethylene oxide or THF and propylene oxide. These are available from BASF as PolyTHF® B, a block copolymer, and PolyTHF® R, a random copolymer. In an embodiment the hydrophobic oligomer is polytetrahydrofuran. In another embodiment, the hydrophobic oligomer is polypropylene glycol. The various polyether polyols generally have a number average molecular weight (Mn) as determined by assay of the terminal functional groups which is an average molecular weight greater than about 700, such as from about 700 to about 10,000, from about 1,000 to about 5,000, or from about 1,000 to about 2,500. In some embodiments, the polyether polyols include a blend of two or more different molecular weight polyethers, such as a blend of 2,000 Mn and 1,000 Mn PTMEG.

Suitable polyesters can include linear polyesters having a number average molecular weight (Mn) of from about 500 to about 10,000, from about 700 to about 5,000, or from about 700 to about 4,000, and generally have an acid number less than 1.3 or less than 0.5. The molecular weight is determined by assay of the terminal functional groups and is related to the number average molecular weight. The polyesters may be produced by (1) an esterification reaction of one or more glycols with one or more dicarboxylic acids or anhydrides or (2) by transesterification reaction, i.e., the reaction of one or more glycols with esters of dicarboxylic acids. Mole ratios generally in excess of more than one mole of glycol to acid are preferred so as to obtain linear chains having a preponderance of terminal hydroxy groups. Suitable polyesters also include various lactones such as polycaprolactone typically made from ε-caprolactone and a bifunctional initiator such as diethylene glycol. The dicarboxylic acids of the desired polyester can be aliphatic, cycloaliphatic, aromatic, or combinations thereof. Suitable dicarboxylic acids which may be used alone or in mixtures generally have a total of from 4 to 15 carbon atoms and include: succinic, glutaric, adipic, pimelic, suberic, azelaic, sebacic, dodecanedioic, isophthalic, terephthalic, cyclohexane dicarboxylic, and the like. Anhydrides of the above dicarboxylic acids such as phthalic anhydride, tetrahydrophthalic anhydride, or the like, can also be used. Adipic acid is a preferred acid. The glycols which are reacted to form a desirable polyester intermediate can be aliphatic, aromatic, or combinations thereof, including any of the glycols described above in the chain extender section, and have a total of from 2 to 20 or from 2 to 12 carbon atoms. Suitable examples include ethylene glycol, 1,2-propanediol, 1,3-propanediol, 1,3-butanediol, 1,4-butanediol, 1,5-pentanediol, 1,6-hexanediol, 2,2-dimethyl-1,3-propanediol, 1,4-cyclohexanedimethanol, decamethylene glycol, dodecamethylene glycol, and mixtures thereof.

Polycaprolactones useful in the technology described herein can include polyester diols derived from caprolactone monomers. The polycaprolactone polyester polyols are terminated by primary hydroxy groups. Suitable polycaprolactone polyester polyols may be made from ε-caprolactone and a bifunctional initiator such as diethylene glycol, 1,4-butanediol, or any of the other glycols and/or diols listed herein. In some embodiments, the polycaprolactone polyester polyols are linear polyester diols derived from caprolactone monomers. Useful examples include CAPA™ 2202A, a 2,000 number average molecular weight (Mn) linear polyester diol, and CAPA™ 2302A, a 3,000 Mn linear polyester diol, both of which are commercially available from Perstorp Polyols Inc. These materials may also be described as polymers of 2-oxepanone and 1,4-butanediol. The polycaprolactone polyester polyols may be prepared from 2-oxepanone and a diol, where the diol may be 1,4-butanediol, diethylene glycol, monoethylene glycol, 1,6-hexanediol, 2,2-dimethyl-1,3-propanediol, or any combination thereof. In some embodiments, the diol used to prepare the polycaprolactone polyester polyol is linear. In some embodiments, the polycaprolactone polyester polyol is prepared from 1,4-butanediol. In some embodiments, the polycaprolactone polyester polyol has a number average molecular weight from 500 to 10,000, or from 500 to 5,000, or from 1,000 or even 2,000 to 4,000 or even 3,000.

Suitable polycarbonates include those prepared by reacting a glycol with a carbonate. U.S. Pat. No. 4,131,731 is hereby incorporated by reference for its disclosure of hydroxy terminated polycarbonates and their preparation. Such polycarbonates are linear and have terminal hydroxy groups with essential exclusion of other terminal groups. The essential reactants are glycols and carbonates. Suitable glycols are selected from cycloaliphatic and aliphatic diols containing 4 to 40, and or even 4 to 12 carbon atoms, and from polyoxyalkylene glycols containing 2 to 20 alkoxy groups per molecule with each alkoxy group containing 2 to 4 carbon atoms. Suitable diols include aliphatic diols containing 4 to 12 carbon atoms such as 1,4-butanediol, 1,5-pentanediol, neopentyl glycol, 1,6-hexanediol, 2,2,4-trimethyl-1,6-hexanediol, 1,10-decanediol, hydrogenated dilinoleylglycol, hydrogenated dioleylglycol, 3-methyl-1,5-pentanediol; and cycloaliphatic diols such as 1,3-cyclohexanediol, 1,4-dimethylolcyclohexane, 1,4-cyclohexanediol, 1,3-dimethylolcyclohexane, 1,4-endomethylene-2-hydroxy-5-hydroxymethyl cyclohexane, and polyalkylene glycols. The diols used in the reaction may be a single diol or a mixture of diols depending on the properties desired in the finished product. Polycarbonate intermediates which are hydroxy terminated are generally those known to the art and in the literature. Suitable carbonates are selected from alkylene carbonates composed of a 5 to 7 member ring. Suitable carbonates for use herein include ethylene carbonate, trimethylene carbonate, tetramethylene carbonate, 1,2-propylene carbonate, 1,2-butylene carbonate, 2,3-butylene carbonate, 1,2-ethylene carbonate, 1,3-pentylene carbonate, 1,4-pentylene carbonate, 2,3-pentylene carbonate, and 2,4-pentylene carbonate. Also, suitable herein are dialkylcarbonates, cycloaliphatic carbonates, and diarylcarbonates. The dialkylcarbonates can contain 2 to 5 carbon atoms in each alkyl group and specific examples thereof are diethylcarbonate and dipropylcarbonate. Cycloaliphatic carbonates, especially dicycloaliphatic carbonates, can contain 4 to 7 carbon atoms in each cyclic structure, and there can be one or two of such structures. When one group is cycloaliphatic, the other can be either alkyl or aryl. On the other hand, if one group is aryl, the other can be alkyl or cycloaliphatic. Examples of suitable diarylcarbonates, which can contain 6 to 20 carbon atoms in each aryl group, are diphenylcarbonate, ditolylcarbonate, and dinaphthylcarbonate.

Polycastor oils may also be employed as the hydrophobic oligomer. Polycastor oil is polymerized castor oil. Unsaturated bonds (C=C) derived from ricinoleic acid in the castor oil molecules are radically polymerized using organic peroxides or the like as an initiator, thereby forming polycastor oil. Polycastor oil has a structure with more branched portions than castor oil, and the number of hydroxy groups in such a fat and oil molecule is larger than that of castor oil. That is to say, polycastor oil has more hydroxy groups that may function as origins of polymerization, and has a structure with more branched portions. Polycastor oils (for example, those available from Vertellus™) can have functionalities of 2 and higher.

The hydrophobic oligomers may also be employed as adducts. Suitable adducts can include, for example, adducts with a lactone, diacid or mixtures thereof.

In one embodiment the hydrophobic oligomer can be a dimer diol (for example, Pripol™ 2030 available from Croda™) with a lactone, diacid or mixture thereof.

The Hard Segments

The hard segments of the structurant polymer can be derived from at least one diisocyanate. Diisocyanates suitable for use in preparing the polymer can include linear, non-branched aliphatic diisocyanates of from about 2 to about 36 carbon atoms, or about 3 to 33 carbon atoms, or even about 4 or 5 to about 27 or 30 carbon atoms. Such diisocyanates can include, but not be limited to, for example, diisocyanatomethane, hexamethylene diisocyanate (HDI), 1,10-decane diisocyanate, 1,4-butane diisocyanate (BDI), 1,12-dodecane diisocyanate, and the like. In some embodiments, the structurant polymer is prepared with a diisocyanate component that includes HDI. In some embodiments, the structurant polymer is prepared with a diisocyanate component that consists essentially of HDI. In some embodiments, the structurant polymer is prepared with a diisocyanate component that consists of HDI.

In some embodiments, the diisocyanate component is essentially free of, or even completely free of, diisocyanates having aromatic or cyclic moieties.

In some embodiments, the diisocyanate component can include other diisocyanates in addition to the linear, non-branched aliphatic diisocyanates, such as, for example, branched diisocyanates, cyclic diisocyanates, aromatic diisocyanates, or mixtures thereof. Branched or cyclic aliphatic diisocyanates were found not to influence intermolecular hydrogen bonding and therefore polymers made exclusively with these diisocyanates did not exhibit thickened oil systems. However, branched or cyclic diisocyanates could be used up to about 50 mole %, or for example, up to about 40 mole %, or up to about 20 or about 30 mole % along with linear unbranched diiocyanates to control the rheological response of the subsequent polymer. In an embodiment, branched or cyclic diisocyanates can be used from about 0.1 to about 50 mole %, or from about 0.5 to about 25 mole %, or from about 1 to about 5 or 10 mole %.

In an embodiment, the hard segment of the structurant polymer can be prepared from a single diisocyanate, and in other embodiments, the hard segment of the structurant polymer can be prepared from a combination of at least two or more diisocyanates.

In addition to the diisocyanate, the hard segment can be derived from at least one chain extending compound. Chain extenders can include short chain (i.e., less than 250 molecular weight) polyols, polyamines, and combination thereof.

Suitable chain extending polyol compounds can include, for example lower aliphatic or short chain glycols having from 2 to 20, or 2 to 12, or 2 to 10 carbon atoms. Suitable examples include ethylene glycol, diethylene glycol, propylene glycol, dipropylene glycol, 1,4-butanediol (BDO), 1,6-hexanediol (HDO), 1,3-butanediol, 1,5-pentanediol, neopentylglycol, 1,4-cyclohexanedimethanol (CHDM), 2,2-bis[4-(2-hydroxyethoxy) phenyl]propane (HEPP), hexamethylenediol, heptanediol, nonanediol, dodecanediol, 3-methyl-1,5-pentanediol, and hydroxyethyl resorcinol (HER), and the like, as well as mixtures thereof. A particular chain extending diol suitable for the organic phase compositions can include the dimer diols available from Croda™ as Pripol™, and particularly, Pripol 2030.

Suitable chain extending polyamine compounds can include lower aliphatic or short chain diamines having from 2 to 20, or 2 to 12, or 2 to 10 carbon atoms. Suitable examples include primary amines such as ethylenediamine, propylenediamine, butanediamine, hexamethylenediamine, and the like, as well as mixtures thereof. Other example polyamine chain extending compound can include secondary amines, such as dimethyl diamine or diphenyl diamine. The chain extender can also include a mixed primary and secondary amines, such as, for example those commercially available as Duomeens™ from AkzoNobel™.

In some embodiments, the chain extender used to prepare the structurant polymer includes a cyclic chain extender. Suitable examples include CHDM, HEPP, HER, and combinations thereof. In some embodiments, the chain extender used to prepare the polymer includes an aromatic cyclic chain extender, for example HEPP, HER, or a combination thereof. In some embodiments, the chain extender used to prepare the polymer includes an aliphatic cyclic chain extender, for example CHDM. In some embodiments, the chain extender used to prepare the polymer is substantially free of, or even completely free of aromatic chain extenders, for example aromatic cyclic chain extenders. In some embodiments, the chain extender used to prepare the polymer is substantially free of, or even completely free of polysiloxanes. In some embodiments, the chain extender used to prepare the polymer include a linear aliphatic chain extender, which can be branched or non-branched. In one embodiment, the chain extender can be a linear non-branched aliphatic chain extender.

In some embodiments, the chain extender component includes 1,4-butanediol, 2-ethyl-1,3-hexanediol, 2,2,4-trimethyl pentane-1,3-diol, 1,6-hexanediol, 1,4-cyclohexane dimethylol, 1,3-propanediol, 3-methyl-1,5-pentanediol or combinations thereof. In some embodiments, the chain extender component includes 1,4-butanediol, 3-methyl-1,5-pentanediol or combinations thereof. In some embodiments, the chain extender component includes 1,4-butanediol. Other chain extenders include amine alcohols such as ethanolamine, propanolamine and the like.

In an embodiment, the hard segment of the structurant polymer can be prepared from a single diisocyanate and a single chain extending compound, and in other embodiments, the hard segment of the structurant polymer can be prepared from a single diisocyanate and a combination of at least two or more chain extending compounds. In an embodiment, the hard segment of the structurant polymer can be prepared from a at least two or more diisocyanates and a single chain extending compound, and in other embodiments, the hard segment of the structurant polymer can be prepared from at least two or more diisocyanates and a combination of at least two or more chain extending compounds.

Other Optional Components of the Structurant Polymer

The structurant polymer may be the simple reaction product of the variously chosen diisocyanates, chain extending compounds, and hydrophobic oligomers. However, the structurant polymer may also contain functional groups or substituents reacted onto the polymer backbone. For example, short chain diols or diamines, triols etc. may be reacted onto the structurant polymer to create increased branching. In addition, the polymer may be terminated, or capped, with the addition of a mono-functional reactant, such as, for example, a monofunctional alcohol, amine, anhydride, or mixture thereof. The addition of functional groups or other substituents along the polymer backbone, as well as the termination of the polymer may be done by well known methods in the art. In a particular embodiment, the polymer can be capped with an alkylamine. Other alcohols considered are $C_1$-$C_{60}$ alkyl alcohols, cholesterol, tocopherol and other alcohols.

One issue that may arise with thickened cosmetic compositions can be the presence of "orange peel" on the inside surface of the container. Orange peel is known in the coating industry and is produced by three factors: high viscosity, poor flow and surface energy mismatch. The structurant polymer may be modified to reduce the presence of such orange peel by reducing the surface tension of the polymer. In an embodiment, a flow improving reactant may be reacted either into the backbone of the structurant polymer or to the ends of the structurant polymer. The flow improving reactant may be, for example, a silicone containing compound or a fluorine containing compound, such as, for example, a reactive silicone di-hydroxy polymer that may be reacted into the structurant backbone (such a dihydroxy-poly(dimethylsiloxane) (e.g. Aldrich)), or a mono-hydroxy silicone (such as poly(dimethylsiloxane) mono-hydroxy (e.g. Aldrich)) that may be reacted onto the chain ends or a fluorine containing polyols such as Polyfox PF-6320 (Omnova). Such flow improvers may also be added simply in admixture with the structurant polymer however, reacting these moieties into the backbone improves clarity of the polymer in oil. Some example flow improvers can include, but not be limited to, polyether modified siloxanes, such as BYK™-349 from Atlanta; phosphate esters of tridecyl alcohol ethoxylate, such as Dexter™ OC-70 from Dexter Chemicals; ethoxylated non-ionic wetters, such as Dynol™

604 from Air Products; alkyl ammonium chloride flourosurfactants, such as Chemguard™ S103A from Chemguard; anionic flourosurfactants, such as Capstone™ FS63 and FS64 from DuPont; ?????, such as Additol™ VXL-4930 from Prospector; polyether siloxane copolymers, such as TegoWet™ 500 from Evonik; polysilicone-16 (and) trideceth-5, such as SilSoft Spread™ SEL from Momentive; dimethicone PEG-7 isostearate, such as SilSense™ DW-18 Silicone, or dimethicone PEG-8 phosphate, such as SilSense™ PE-100 Silicone, or PEG-7 amodimethicone, such as SilSense™ A-21 Silicone, all from Noveon; flourosurfactant diols, such as PolyFox™ 636 or 6520 from Omnova; poly(dimethylsiloxane)-mono; poly(dimethylsiloxane)hydroxyl terminated; or fluoroaliphatic surfactants, such as Masurf™ FS-3240 from Pilot.

Organic Phase Compositions

The inventors have found that an organic phase can be thickened or gelled by adding to the organic phase a structurant polymer specifically formulated to the organic phase. The formulating of the structurant polymer can be achieved, for example, by taking into account 1) the constituent parts of the organic phase, such as the various triglycerides, esters, waxes, etc., that might be in the organic phase, and 2) preparing a structurant polymer having constituent parts (e.g., the hydrophobic oligomer, the diisocyanate, and the other optional components that might be in the structurant polymer) that synergistically interact with the constituent parts of the organic phase.

The Organic Phase

The organic phase is generally a hydrocarbon, such as an oil, but may include emollients, fragrances and the like. In essence, the organic phase is any organic material in which a structurant polymer is miscible.

Non-limiting examples of an organic phase include mineral oils; petrolatums; vegetable oils (including nut oils); hydrogenated vegetable oils; essential oils; algae oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); and polyalkylene glycols; lanolin and lanolin derivatives; waxes; and the like, as well as mixtures thereof. The organic phase can be utilized in an amount of greater than about 75 wt. % by weight of the total composition in one aspect, greater than 80 wt. % in another aspect, or greater than 85 or 90 wt. % in a further aspect.

Mineral oils and petrolatums include cosmetic, USP and NF grades and are commercially available from Penreco under the Drakeol™ and Penreco™ trade names.

Exemplary vegetable oils suitable as an organic phase can include but are not limited to peanut oil, sesame oil, avocado oil, coconut oil, cocoa butter, almond oil, safflower oil, corn oil, cotton seed oil, castor oil, olive oil, jojoba oil, palm oil, palm kernel oil, soybean oil, wheat germ oil, linseed oil, sunflower seed oil; and the mono-, di-, and triglycerides thereof, and hydrogenated derivatives thereof; and mixtures thereof. Exemplary mono-, di- and triglycerides are, for example, caprylic triglyceride, capric triglyceride, caprylic/capric triglyceride, and caprylic/capric/lauric triglyceride, caprylic/capric/stearic triglyceride, and caprylic/capric/linoleic triglyceride.

Ethoxylated mono- and diglycerides of the foregoing vegetable oils are also contemplated, such as, for example, PEG-8 Caprylic/Capric Glycerides.

Essential oils can be employed as an organic phase and can encompass oils having an aromatic essence. Essential oils include, but are not limited to peppermint oil, cedar oil, castor oil, clove oil, geranium oil, lemongrass oil, linseed oil, mint oil, thyme oil, rosemary oil, cornmint oil (*Mentha arvensis*), garlic oil, anise oil, basil oil, camphor oil, citronella oil, *eucalyptus* oil, fennel oil, ginger oil, grapefruit oil, lemon oil, lime oil, mandarin oil, orange oil, pine needle oil, pepper oil, rose oil, tangerine oil, tea tree oil, tea seed oil, mineral oil and fish oil.

Suitable fatty alcohol an organic phase include but are not limited to fatty alcohols containing 8 to 50 carbon atoms. Exemplary fatty alcohols include capryl alcohol, pelargonic alcohol, capric alcohol, lauryl alcohol, myristyl alcohol, cetyl alcohol, isocetyl alcohol, stearyl alcohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acids as the organic phase include but are not limited to fatty acids containing 10 to 50 carbon atoms. Exemplary fatty acids are selected from capric acid, lauric acid, myristic acid, palmitic acid, stearic acid, oleic acid, linoleic acid, arachidic acid, behenic acid, and mixtures thereof.

Suitable fatty acid and fatty alcohol ester organic phases include but are not limited to hexyl laurate, decyl oleate, isopropyl stearate, isopropyl isostearate, butyl stearate, octyl stearate, ethylhexyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, isostearyl hydroxy stearate, diisostearyl fumarate, lauryl lactate, diethyl hexyl maleate, PPG-14 butyl ether and PPG-2 myristyl ether propionate, ethylhexyl octanoate, cetearyl octanoate, cetearyl ethylhexanoate, and mixtures thereof.

Alkoxylated fatty alcohols are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect the ethoxylated fatty alcohols can be represented by the formula R—$(OCH_2CH_2)_n$—OH wherein R represents the linear or branched aliphatic residue of the parent fatty alcohol and n represents the number of molecules of ethylene oxide. In another aspect, R is derived from a fatty alcohol containing 8 to 40 carbon atoms. In one aspect n is an integer ranging from 2 to 100, 3 to 80 in another aspect, and 3 to 50 in a further aspect. In a still further aspect, R is derived from a fatty alcohol organic phase set forth above. Exemplary ethoxylated fatty alcohols can include but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and ethoxylated/propoxylated adducts of the foregoing fatty alcohols are also contemplated. More specific examples of alkoxylated alcohols are beheneth 5-30 (the 5-30 meaning the number of repeating ethylene oxide or propylene oxide units), Ceteareth 2-100, Ceteth 1-45, Cetoleth 24-25, Choleth 10-24, Coceth 3-10, C9-11 Pareth 3-8, C11-15 pareth 5-40, C11-21 Pareth 3-10, C12-13 Pareth 3-15, Deceth 4-6, Dodoxynol 5-12, Glycereth 7-26, Isoceteth 10-30, Isodeceth 4-6, Isolaureth 3-6, Isosteareth 3-50, Laneth 5-75, Laureth 1-40, Nonoxynol 1-120, Nonoxynol 5-150, Octoxynol 3-70, Oleth 2-50, Steareth 2-100, Trideceth 2-10, and so on.

Alkoxylated fatty acids are formed when a fatty acid is reacted with an alkylene oxide or with a pre-formed polymeric ether. The resulting product may be a monoester, diester, or mixture thereof. Suitable ethoxylated fatty acid ester organic phases suitable for use are products of the addition of ethylene oxide to fatty acids. The product is a polyethylene oxide ester of a fatty acid. In one aspect, the ethoxylated fatty acid esters can be represented by the formula $R-C(O)O(CH_2CH_2O)_n-H$, wherein R represents the linear or branched aliphatic residue of a fatty acid and n represents the number of molecules of ethylene oxide. In another aspect, n is an integer ranging from 2 to 50, 3 to 25 in another aspect, and 3 to 10 in a further aspect. In still another aspect, R is derived from a fatty acid containing 8 to 30 carbon atoms. In a still further aspect, R and the C(O)O— group is derived from a fatty acid organic phase material set forth above. It is to be recognized that propoxylated and ethoxylated/propoxylated products of the foregoing fatty acids are also contemplated. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Benzoate ester organic phases are selected from but not limited to $C_{12}$ to $C_{15}$ alkyl benzoate, isostearyl benzoate, octyl dodecyl benzoate, stearyl benzoate, dipropylene glycol dibenzoate, methyl gluceth-20 benzoate, castor oil benzoate, cetyl ricinoleate benzoate, ethylhexyl hydroxystearate benzoate, dimethicone PEG/PPG-20/23 benzoate, and dimethicone PEG-8 benzoate.

Guerbet ester organic phase materials are formed from the esterification reaction of a Guerbet alcohol with a carboxylic acid. Guerbet ester organic phase materials are commercially available from Noveon, Inc. as G-20, G-36, G-38, and G-66.

Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from Noveon, Inc. under the following trade names Lanolin LP 108 USP, Lanolin USP AAA, Acetulan™, Ceralan™, Lanocerin™, Lanogel™ (product designations 21 and 41), Lanogene™, Modulan™, Ohlan™, Solulan™ (product designations 16, 75, L-575, 98, and C-24), Vilvanolin™ (product desginations C, CAB, L-101, and P).

Waxes include those derived from plant, animal/insect, mineral, petroleum and synthetic sources. Synthetically modified natural (plant and animal/insect) waxes are also contemplated. Exemplary plant derived waxes include but are not limited to bayberry wax, candelilla wax, hydrolyzed candelilla wax, carnauba wax, ethoxylated carnauba wax (e.g., PEG-12 carnauba wax), hydrolyzed carnauba wax, carnauba acid wax, hydrogenated castor wax, esparto wax, hydrogenated Japan wax, hydrogenated jojoba oil, jojoba oil esters, sulfurized jojoba oil, ouricury wax, palm kernel wax, and hydrogenated rice bran wax. Exemplary animal/insect derived waxes include but are not limited to beeswax, oxidized beeswax, ethoxylated beeswax (e.g., PEG-6 beeswax, PEG-8 beeswax, PEG-12 beeswax, PEG-20 beeswax), dimethicone copolyol beeswax esters and dimethiconol beeswax ester (e.g. Bis-Hydroxyethoxypropyl Dimethicone Beeswax Esters, Dimethicone PEG-8 Beeswax, and Dimethiconol Beeswax available from Noveon, Inc. under the Ultrabee™ trademark), Chinese wax, shellac wax, spermaceti wax, mink wax, and lanolin wax. Exemplary mineral waxes include but are not limited to ceresin waxes, montan wax, montan acid wax, and ozocerite. Exemplary petroleum waxes include paraffin waxes, such as isododecane and isohexadecane, microcrystalline waxes, and oxidized microcrystalline waxes. Exemplary synthetic waxes include synthetic beeswax, synthetic candelilla wax, synthetic carnauba wax, synthetic Japan wax, synthetic jojoba oil, polyolefin waxes (e.g., polyethylene wax), ethylene glycol diesters or triesters of fatty acids containing 18 to 40 carbon atoms. Mixtures of two or more of the forgoing waxes and classes of waxes are also contemplated.

In some embodiments, the organic phase material can be an emollient such as dioctyl/dicapryl ether.

In some embodiments, the organic phase material can be an organic sunscreen.

The organic phase material can also be a fragrance, whether naturally derived or synthetically derived.

In some embodiments, the oil comprises, consists essentially of, or consists of a mineral oil. In other embodiments, the oil comprises, consists essentially of, or consists of a vegetable oil.

In some embodiments, the organic phase material can be any of the common oils employed in cosmetic formulations, such as, for example, castor oil, cocoglycerides (di, tri), caprylic/capric triglyceride, coconut oil, sweet almond oil, sunflower oil, isopropyl palmitate, cetearyl ethylhexanoate, ethylhexyl stearate, jojoba oil, isododecane, mineral oil, isohexadecane, dioctyl/dicapryl ether, or mixtures thereof.

It will be recognized by those of skill in the art that the various organic phase materials mentioned above may be considered in various categories. Thus, the exemplary descriptions of the various organic phase materials is not meant as a single definition of any one specific organic phase material. There are many more organic phase materials not referenced herein, but nonetheless would be expected to be suitable as an organic phase hereunder when employing the formulating principles set forth herein. In addition, the organic phase materials may be used alone or in combination with other organic phase materials.

Clarity

A starting point for determining the appropriate structurant polymer for a chosen organic phase material can be to determine the desired clarity of the composition. To achieve a clear composition for a given organic phase, hydrophobic oligomers that are soluble in the chosen organic phase can be employed as a constituent part of the structurant polymer. The determination of solubility of hydrophobic oligomers in the organic phase can be achieved empirically, for example, by measuring the clarity of the solution. Clarity can be measured by several methods. One example method for measuring clarity can encompass employing a reflectance probe (such as a Brinkman PC950 colorimeter) to measure the average light transmission of the sample, and comparing the average transmission to the transmission of a standard filtered neat oil. Another method can include visually comparing the sample to a scale of samples having varying clarity. For example, a number of standard samples can be prepared with varying amounts of scattering in the oil of interest. The standard samples can be graded from 1 (poor) to 5 (excellent) and the reference sample can subsequently be graded in comparison to the standard samples.

In addition, a method of determining the solubility of hydrophobic oligomers in the organic phase can be to compare the Hansen Solubility Parameters ("HSP") of the hydrophobic oligomers with the HSP of the chosen organic phase. The HSP includes a dispersive parameter "$\delta D$," a polar parameter "$\delta P$," and a hydrogen bonding parameter "$\delta H$." The comparison between the different parameters of the organic phase and the hydrophobic oligomers can be designated as the $\Delta HSP_{o-p}$, and can be calculated according to Formula I:

$$\Delta HSP_{o-p} = \sqrt{\{4(\delta D_o - \delta D_p)^2 + (\delta P_o - \delta P_p)^2 + (\delta H_o - \delta H_p)^2\}} \quad \text{Formula I}$$

where the respective $\epsilon D$, $\delta P$ and $\delta H$ parameters encompass both single values and the average of the parameters for all materials in the respective mixtures.

In some cases the HSP of the organic phase and/or hydrophobic oligomers can be extracted from the literature, and in others the HSP can be estimated from software developed by S. Abbott, C. Hansen and H. Yamamoto (www.hansen-solubility.com). The smaller the $\Delta HSP_{o-p}$, the more likely the hydrophobic oligomers will be soluble in the chosen organic phase, and thereby the clearer the composition is likely to be. For a clear composition, the $\Delta HSP_{o-p}$ can be less 4, or less than 2, and in some cases 1 or less or 0.5 or less. If clarity is not a required property of the composition, the $\Delta HSP_{o-p}$ can also be 4 or greater. However, if the $\Delta HSP_{o-p}$ is too high (>8), then the polymer will be minimally soluble in the oil and therefore will not thicken.

In another embodiment, solubility of the polymer can be deduced from the solubility of the oligomer simply by measuring the solubility of the oligomer. Solubility of the oligomer can be found, for example, by dissolving up to 50 wt % of the oligomer of interest in 50 wt % oil of interest and heating the mixture to 80° C. for 12-16 hours in an oven with intermittent stirring. After allowing the sample to cool to room temperature, the solubility can be assessed qualitatively. If the solution is completely clear, the oligomer can be considered to be completely soluble. If the solution is cloudy or separated, the process can be repeated with a reduced amount of the oligomer concentration (for example, in steps of 5 wt %) until a clear solution is obtained. The oligomer solubility is reported as the highest concentration that gave a clear solution.

Thickening/Gelling

To achieve a thickened or gelled composition, it has been found that the distance between diisocyanate moieties along the structurant polymer backbone can have an effect on the thickening or gelling efficiency of the polymer within the chosen organic phase. In general, the closer the diisocyanates moieties are spaced relative to neighboring diisocyanates along the polymer backbone, the better the thickening efficiency of the polymer in the organic phase. The largest contributor to the spacing of the diisocyanate moieties on the polymer backbone can be the hydrophobic oligomer. Thus, the hydrophobic oligomers in the polymer can be chosen by molecular weight to minimize the spacing between diisocyanate moieties. In an embodiment of the technology, the molecular weight of the hydrophobic oligomers can be, on average, less than about 2,000, or less than about 1,500, or less than 1,250, or even less than about 1,000. In some embodiments, the average molecular weight of the oligomers in the polymer can be between about 500 and about 2,000, or about 500 to about 1,500, or between about 750 and about 1,250, or from about 250 to about 1,000. By average molecular weight, it is meant is the sum of the molecular weights of the oligomers divided by the total number of oligomers.

In an embodiment, the polymer can optionally contain chain extending components. Chain extending components are generally short chain compounds, such as, for example, short chain diols or short chain diamines. The use of such chain extending compounds can serve to intermittently replace the oligomers along the polymer backbone. Where the chain extending component replaces the oligomer, the respective diisocyanate moieties will necessarily be closer together. Thus, the use of chain extending components can be employed to affect the thickening efficiency of the polymer in a particular organic phase. As a result, the use of chain extending components can allow for higher molecular weight oligomers in the polymer backbone. In such cases that a chain extending component is employed in the polymer, the average molecular weight of the oligomers can be on average, less than about 6,000, such as, for example, less than 4,500, or less than about 3,000, or less than about 2,500, or even less than about 2,000. In some embodiments, the average molecular weight of the oligomers in the polymer can be between about 500 and about 3,000, or between about 750 and about 2,500, or from about 250 to about 2,000.

In addition to controlling the molecular weight of the oligomer, the ratio of the hydrogen bonding donors ($H_d$) to hydrogen bonding acceptors ($H_a$) in the polymer/organic phase can be controlled. In particular, the ratio of $H_d/H_a$ can be 1 or greater, or greater than 1. The $H_d$ and $H_a$ of the system can be determined by inventorying the constituent parts of both the organic phase and the polymer, and taking the summation of the total $H_d$ and $H_a$ between the two. Where the $H_d/H_a$ is less than 1, or 1 or less. $H_d$ can be increased by adding more polymer to the system.

For example, consider a theoretical polyurethane prepared from a di-functional oligomer of about 1,500 molecular weight, and a diisocyanate, which provides a polymer of about 15,000 molecular weight. Each oligomer is di-functional and therefore has 2 hydrogen bonding acceptors. Likewise, each diisocyanate is di-functional and has 2 hydrogen bond donors. Based on the stoichiometry to achieve a 15,000 molecular weight polymer, the polymer will have an oligomer/diisocyanate ratio of about 10/11. Thus, the total $H_d$ for the polymer will be about 22, that is, 11 diisocyanates having 2 donors each. By comparison, if the oligomer was replaced with a lower molecular weight oligomer (for example, 1,000) then, at the same polymer molecular weight (~15,000), the number of donor sites would be larger (2×16=32).

For most solvents (e.g., oil or emollient), the $H_d/H_a$ is generally nearly zero since such materials are generally based on esters of fatty acids. For example, for isopropyl palmitate ("IPP"), $H_d$ is 0 and $H_a$ is 2, such that $H_d/H_a$ is 0 for each IPP molecule. On a molecule-to-molecule basis, the theoretical polymer to IPP will provide an $H_d/H_a$ ratio of about 11 excess donors (i.e., 22 from the polymer and 2 from the IPP for 22/2=11). Since the molecular weight of the IPP is about 50 times less than the polymer and the polymer concentration in solution is much less than the IPP (say 5 wt %), the effective $H_d/H_a$ would be approximately $10^{-2}$ and it would not be expected that the polymer would thicken at this concentration unless some driving force, such as phase separation occurred.

The total concentration of polymer in the organic phase can be up to 10 wt %, or up to 8 wt %, or up to 6 wt %. In some embodiments, the total concentration of polymer in the organic phase can be from about 0.1 to about 10 wt %, or from about 0.1 or 0.5 to about 5 or 6 wt %, and even from about 1 to about 3 or 4 wt %.

In the case of adding an amine, whether as the hydrophobic oligomer or as a chain extending compound, urea linkages can be formed rather than urethane linkages. The use of urea linkages in the structurant polymers should be done with caution since ureas are more polar moieties than urethanes and can reduce the clarity and solubility of the polymer in the organic phase. However, judicious use of urea can also increase the efficiency and produce a higher gel strength in the oil formulation as such urea linkages increase the number of $H_a$ in the composition.

The rheology of the compositions can be determined by measuring the storage modulus (G') and loss modulus (G") of a sample, which are commonly reported in Pascals (Pa). G' describes the elastic or solid-like properties of a sample. The higher the G' value, the more elastic or solid-like the sample will be. G" describes the viscous or fluid-like properties of the sample. The higher the G", the more fluid-like the sample will be. Where G' is greater than G", the sample will behave in a more elastic or solid-like manner, and where G" is greater than G', the sample will behave in a more fluid-like or viscous manner. Both G' and G" can be determined by employing standard rheometric techniques.

Other Additives

The organic phase compositions can additionally contain other additives, or the organic phase compositions can be employed in a fully formulated composition alongside other additives. Other additives can include, for example, additives commonly found in personal care, home care, health care, and/or institutional and industrial care compositions.

The term "personal care products" as used herein includes, without being limited thereto, cosmetics, toiletries, cosmeceuticals, beauty aids, insect repellents, personal hygiene and cleansing products applied to the body, including the skin, hair, scalp, and nails of humans and animals.

The term "home care products" as used herein includes, without being limited thereto, products employed in a domestic household for surface cleaning or maintaining sanitary conditions, such as in the kitchen and bathroom (e.g., hard surface cleaners, hand and automatic dish care, toilet bowl cleaners and disinfectants), and laundry products for fabric care and cleaning (e.g., detergents, fabric conditioners, pre-treatment stain removers), and the like.

The term "health care products" as used herein includes, without being limited thereto, pharmaceuticals (controlled release pharmaceuticals), pharmacosmetics, oral care (mouth and teeth) products, such as oral suspensions, mouthwashes, toothpastes, dentifrices, and the like, and over-the-counter products and appliances (topical and transdermal), such as patches, plasters and the like, externally applied to the body, including the skin, scalp, nails and mucous membranes of humans and animals, for ameliorating a health-related or medical condition, for generally maintaining hygiene or well-being, and the like.

The term "institutional and industrial care" ("I&I") as used herein includes, without being limited thereto, products employed for surface cleaning or maintaining sanitary conditions in institutional and industrial environments, textile treatments (e.g., textile conditioners, carpet and upholstery cleaners), automobile care (e.g., hand and automatic car wash detergents, tire shines, leather conditioners, liquid car polishes, plastic polishes and conditioners), paints and coatings, and the like.

For example, the oil compositions can include, Pharmaceutical and Cosmeceutical acitves; Opacifying/Pearlescent Materials; Opacifiers; Particulates; Botanicals; Preservatives; Auxiliary Rheology Modifier; Chelating Agents; Auxiliary Solvents and Diluents; Fragrances; Surfactants; silicone fluids (e.g., volatile silicone oils and non-volatile silicone oils); Organic and Inorganic UV Filters, and Emollients; among others.

Pharmaceutical and Cosmeceutical Actives

The organic phase compositions can be formulated with a pharmaceutical and/or a cosmeceutical active to deliver a desired effect. Examples of such active ingredients include, but are not limited to, caffeine, vitamin C, vitamin D, vitamin E, anti-stretch mark compounds, astringents (e.g., alum, oatmeal, yarrow, witch hazel, bayberry, and isoinvinvepropyl alcohol), draining compounds, depilatories (e.g., calcium and sodium hydroxide, calcium or sodium thioglycolate, or mixtures thereof), hair growth promoting compounds (e.g., monoxidil), skin and hair nourishing compounds, skin and hair protecting compounds, self-tanning compounds (e.g., mono- or polycarbonyl compounds such as, for example, isatin, alloxan, ninhydrin, glyceraldehyde, mesotartaric aldehyde, glutaraldehyde, erythrulose, tyrosine, tyrosine esters, and dihydroxyacetone), UV absorbers (e.g., ethylhexyl methoxy cinnamate, octinoxate, octisalate, oxybenzone), skin lighteners (e.g., kojic acid, hydroquinone, arbutin, fruital, vegetal or plant extracts, such as lemon peel extract, chamomile, green tea, paper mulberry extract, and the like, ascorbyl acid derivatives, such as ascorbyl palmitate, ascorbyl stearate, magnesium ascorbyl phosphate, and the like), lip plumping compounds, anti-aging, anti-cellulite, and anti-acne compounds (e.g., acidic agents such as alpha-hydroxy acids (ANAs), beta-hydroxy acids (BHAs), alpha amino-acids, alpha-keto acids (AKAs), acetic acid, azelaic acid, and mixtures thereof), anti-inflammatory compounds (e.g., aspirin, ibuprofen, and naproxen), analgesics (e.g., acetaminophen), antioxidant compounds, antiperspirant compounds (e.g., aluminum halides, aluminum hydroxyhalides, aluminum sulfate, zirconium (zirconyl) oxyhalides, zirconium (zirconyl)hydroxyhalides, and mixtures or complexes thereof), deodorant compounds (e.g., 2-amino-2-methyl-1-propanol (AMP), ammonium phenolsulfonate; benzalkonium chloride; benzethonium chloride, bromochlorophene, cetyltrimethylammonium bromide, cetyl pyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarban, triclosan, zinc phenolsulfonate, zinc ricinoleate, and mixtures thereof); and suitable mixtures of any of the above.

Opacifying/Pearlescent Materials

Some formulations are often opacified by deliberately incorporating pearlescent materials therein to achieve a cosmetically attractive pearl-like appearance, known as pearlescence. An opacifier often is included in a composition to mask an undesirable aesthetic property, such as to improve the color of a composition that is darkened due to the presence of a particular ingredient, or to mask the presence of particulate matter in the composition. Opacifiers also are included in compositions to improve the aesthetics and consumer acceptance of an otherwise esthetically unpleasing composition. For example, an opacifier can impart a pearlescent appearance to a clear composition, thereby communicating an appearance of creaminess, mildness and body to the consumer. Persons skilled in the art are aware of problems faced by formulators in consistently preparing a stable pearlescent formulation. A detailed discussion is found in the article "Opacifiers and pearling agents in shampoos" by Hunting, Cosmetic and Toiletries, Vol. 96, pages 65-78 (July 1981), incorporated herein by reference.

The opacifying or pearlescent material includes ethylene glycol monostearate, ethylene glycol distearate, polyethylene glycol distearate, stearic alcohol, bismuth oxychloride coated mica, mica coated metal oxides (e.g., titanium dioxide, chromium oxide, iron oxides), myristyl myristate, guanine, glitter (polyester or metallic), and mixtures thereof. Other pearlescent materials can be found in U.S. Pat. Nos. 4,654,207, 5,019,376, and 5,384,114, which are herein incorporated by reference.

An opacifier can be selected from a number of different chemical classes including inorganic compounds, e.g., various aluminum and magnesium salts, and organic compounds, like fatty alcohols, fatty esters and various polymers and copolymers. A representative listing of opacifiers is found in the CTFA Cosmetic Ingredient Handbook, J. Nikitakis, ed., The Cosmetic, Toiletry and Fragrance Association, Inc., Washington, D.C., 1988, at page 75.

In one aspect, the amount of the pearlescent material can be used in amounts ranging from about 0.05% to about 10% by weight, and from about 0.1% to about 3% by weight in another aspect, based upon the total weight of the organic phase composition.

Particulates

Numerous other substantially insoluble compounds and components which require stabilization and/or suspension can be utilized in the organic phase compositions. Examples of such other insoluble compounds include pigments, exfoliants, and anti-dandruff agents.

Exemplary pigments are metal compounds or semi-metallic compounds and may be used in ionic, nonionic or oxidized form. The pigments can be in this form either individually or in a mixture or as individual mixed oxides or mixtures thereof, including mixtures of mixed oxides and pure oxides. Examples are the titanium oxides (e.g., $TiO_2$), zinc oxides (e.g., ZnO), aluminum oxides (for example, $Al_2O_3$), iron oxides (for example, $Fe_2O_3$), manganese oxides (e.g., MnO), silicon oxides (e.g., $SiO_2$), silicates, cerium oxide, zirconium oxides (e.g., $ZrO_2$), barium sulfate ($BaSO_4$), and mixtures thereof.

Numerous cosmetically useful particulate exfoliating agents are known in the art, and the selection and amount is determined by the exfoliating effect desired from the use of the composition, as recognized by those skilled in the cosmetic arts. Useful exfoliating agents include, but are not limited to, natural abrasives, inorganic abrasives, synthetic polymers, and the like, and mixtures thereof. Representative exfoliants include, but are not limited to, ground or powdered pumice, stone, zeolites, nut shells (e.g., almond, pecan, walnut, coconut, and the like), nut meals (e.g., almond, and the like), fruit pits (e.g., apricot, avocado, olive, peach, and the like), hulls, seed and kernel (e.g., oat bran, corn meal, rice bran, grape seed, kiwi seed, wheat, jojoba seed, loofah seed, rose hip seed, and the like), plant matter (e.g., tea tree leaves, corn cob, fruit fibers, seaweed, loofah sponge, microcrystalline cellulose, and the like), bivalve shells (oyster shell, and the like), calcium carbonate, dicalcium pyrophosphate, chalk, silica, kaolin clay, silicic acid, aluminum oxide, stannic oxide, sea salt (e.g., Dead Sea salt), talc, sugars (e.g., table, brown, and the like), polyethylene, polystyrene, microcrystalline polyamides (nylons), microcrystalline polyesters, polycarbonates, and stainless steel fibers. The foregoing exfoliants can be used in the form of granules, powders, flours, and fibers.

Any suitable anti-dandruff agent can be employed in the organic phase compositions. Exemplary anti-dandruff agents include, but are not limited to, sulfur, zinc pyrithione, zinc omadine, miconazole nitrate, selenium sulfide, piroctone olamine, N,N-bis(2-hydroxyethyl)undecenamide, cade oil, pine tar, *Allium cepa* extract *Picea abies* extract, and Undecyleneth-6, and the like, and mixtures thereof.

Other particulates suitable for use in the present compositions include clay, swellable clay, laponite, gas bubbles, liposomes, microsponges, cosmetic beads and flakes. Cosmetic beads, flakes and capsules can be included in a composition for aesthetic appearance or can function as micro- and macro-encapsulants for the delivery of benefit agents to the skin and hair. Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.).

In one aspect, the amount of particulate component can range from about 0.1% to about 10% by weight based on the total weight of the composition.

Botanicals

Optionally, the organic phase compositions can be formulated with botanical material extracts. Extracted botanical materials can include any water soluble or oil soluble material extracted from a particular plant, fruit, nut, or seed. In one aspect, the botanical actives are present in an amount ranging from about 0.1% to about 10% by weight, from about 0.5% to about 8% by weight in another aspect, and from about 1% to about 5% by weight in a further aspect, based of the total weight of the composition.

Suitable botanical agents can include, for example, extracts from Echinacea (e.g., sp. *angustifolia, purpurea, pallida*), *yucca glauca*, willow herb, basil leaves, Turkish oregano, carrot root, grapefruit, fennel seed, rosemary, tumeric, thyme, blueberry, bell pepper, blackberry, *spirulina*, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, *arnica*, centella *asiatica*, cornflower, horse chestnut, ivy, magnolia, oat, pansy, skullcap, seabuckthorn, white nettle, and witch hazel. Botanical extracts include, for example, chlorogenic acid, glutathione, glycrrhizin, neohesperidin, quercetin, rutin, morin, myricetin, absinthe, and chamomile.

Preservatives

In one aspect, any preservative suitable for use in personal care, home care, health care, and institutional and industrial care products, can be used in the organic phase compositions. Suitable preservatives include polymethoxy bicyclic oxazolidine, methyl paraben, propyl paraben, ethyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds disclosed above (e.g., Polyquaternium-1).

In another aspect, acid based preservatives are useful in the organic phase compositions. Any acid based preservative that is useful in personal care, home care, health care, and institutional and industrial care products can be used in the organic phase compositions. In one aspect the acid preservative is a carboxylic acid compound represented by the formula: $R^{53}C(O)OH$, wherein $R^{53}$ represents hydrogen, a saturated and unsaturated hydrocarbyl group containing 1 to 8 carbon atoms or $C_6$ to $C_{10}$ aryl. In another aspect, $R^{53}$ is selected from a hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, and benzoic acid, and mixtures thereof.

The preservatives typically comprise from about 0.01% to about 3.0% by weight in one aspect, from about 0.1% to about 1% by weight in another aspect, and from about 0.3% to about 1% by weight in a further aspect, of the total weight of the personal care organic phase compositions.

Auxiliary Rheology Modifiers

In another aspect, the organic phase compositions can be formulated with one or more rheology modifiers and thickeners. Suitable rheology modifiers and thickeners can include, for example, silica and waxes.

Emulsifiers

Emulsifiers when employed in the organic phase compositions include, but are not limited to, the $C_{12}$-$C_{22}$ fatty alcohols, $C_{12}$-$C_{22}$ alkoxylated alcohols, $C_{12}$-$C_{22}$ fatty acids, $C_{12}$-$C_{22}$ alkoxylated fatty acids (the alkoxylates each having 10 to 80 units of ethylene oxide, propylene oxide, and combinations of ethylene oxide/propylene oxide present in the molecule), $C_8$-$C_{22}$ APGs, ethoxylated sterols (wherein the number of ethylene oxide units ranges from 2 to about 150), partial esters of polyglycerols, esters and partial esters of polyols having 2 to 6 carbon atoms, partial esters of polyglycerols, and organosiloxanes, and combinations thereof.

The $C_8$-$C_{22}$ alkyl APG emulsifiers are prepared by reacting glucose or an oligosaccharide with primary fatty alcohols having 8 to 22 carbon atoms, and comprise a glucosidically bonded $C_8$-$C_{16}$ alkyl group on an oligoglucoside residue whose average degree of oligomerization is 1 to 2. In addition to the APGs described as surfactants above, APGs are available under the trademark Plantacare™ (Cognis Corporation, Cincinnati, Ohio). Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Emulsifiers based on the esters and partial esters of polyols having 2 to 6 carbon atoms are condensed with linear saturated and unsaturated fatty acids having 12 to 30 carbon atoms are, for example, the monoesters and diesters of glycerol or ethylene glycol or the monoesters of propylene glycol with saturated and unsaturated $C_{12}$-$C_{30}$ fatty acids.

Exemplary fatty alcohols and fatty acids, as well as their alkoxylates, the partial esters of polyglycerols, as well as the organosiloxanes are described above.

Chelating Agents

Chelating agents can be employed to stabilize the personal care, home care, health care, and institutional care organic phase compositions against the deleterious effects of metal ions. When utilized, suitable chelating agents include EDTA (ethylene diamine tetraacetic acid) and salts thereof such as disodium EDTA, citric acid and salts thereof, cyclodextrins, and the like, and mixtures thereof. Such suitable chelators typically comprise about 0.001 wt. % to about 3 wt. %, preferably about 0.01 wt. % to about 2 wt. %, and more preferably about 0.01 wt. % to about 1 wt. % of the total weight of the personal care organic phase compositions.

Auxiliary Solvents and Diluents

The personal care, home care, health care, and institutional care compositions of the organic phase compositions in combination with one or more of the foregoing active ingredients and/or with the one or more additives and/or adjuvants, conventionally or popularly included in personal care, health care, home care, and institutional care products discussed above can be prepared as water-free or water-based formulations, and formulations containing water-miscible auxiliary solvents and/or diluents, but are not limited thereto. Useful solvents commonly employed are typically liquids, such as water (deionized, distilled or purified), alcohols, fatty alcohols, polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched alcohols, such as ethanol, propanol, isopropanol, hexanol, and the like; aromatic alcohols, such as benzyl alcohol, cyclohexanol, and the like; saturated $C_{12}$ to $C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$ to $C_4$ alkoxylated alcohols and $C_2$ to $C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents or diluents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$ to $C_{40}$ isoparaffins, alkyl carboxylic esters, such as ethyl acetate, amyl acetate, ethyl lactate, and the like, jojoba oil, shark liver oil, and the like. Some of the foregoing non-aqueous auxiliary solvents or diluents may also be conditioners and emulsifiers.

Scents and Fragrances

The organic phase composition may be formulated with scents and fragrances. The range of the natural odorants includes, in addition to readily volatile, also moderately and only slightly volatile components. The synthetic odorants embrace representatives from practically all classes of odorant substances. The following list comprises examples of known odorants which may be employed with the organic phase compositions, without being limited thereto:

natural products such as tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmine oil, ylang-ylang oil, etc.; alcohols: farnesol, geraniol, linalool, nerol, phenylethyl alcohol, rhodinol, cinnamic alcohol, (Z)-hex-3-en-1-ol, menthol, a-terpineol, etc.; aldehydes such as citral, alpha-hexyl cinnamaldehyde, Lilial, methylionone, verbenone, nootkatone, geranylacetone, etc.; esters such as allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, etc.; lactones such as gamma-undecalactone, delta-decalactone, pentadecanolide, 12-oxahexadecanolide, etc.; acetals such as Viridine (phenylacetaldehyde dimethylacetal), etc.; and other components often used in perfumery such as indole, p-mentha-8-thiol-3-one, methyleugenol, eugenol, anethol, etc.

Surfactants

Suitable surfactants that can be employed with the organic phase compositions can include anionic, cationic, amphoteric, and nonionic surfactants, as well as mixtures thereof. Such compositions are useful in personal care cleansing compositions that contain various components such as substantially insoluble materials requiring suspension or stabilization (e.g., a silicone, an oily material, a pearlescent material, aesthetic and cosmeceutical beads and particles, gaseous bubbles, exfoliants, and the like).

The anionic surfactant can be any of the anionic surfactants known or previously used in the art of aqueous surfactant compositions. Suitable anionic surfactants include but are not limited to alkyl sulfates, alkyl ether sulfates, alkyl sulphonates, alkaryl sulfonates, .alpha.-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect, from 8 to 22 carbon atoms in another aspect and from about 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myritstyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

Suitable classes of cationic surfactants include but are not limited to alkyl amines, alkyl imidazolines, ethoxylated amines, quaternary compounds, and quaternized esters. In addition, alkyl amine oxides can function as a cationic surfactant at a low pH.

Alkylamine surfactants can be salts of primary, secondary and tertiary fatty $C_{12}$-$C_{22}$ alkylamines, substituted or unsubstituted, and substances sometimes referred to as "amidoamines." Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Non-limiting examples of amidoamines and salts thereof include stearamido propyl dimethyl amine, stearamidopropyl dimethylamine citrate, palmitamidopropyl diethylamine, and cocamidopropyl dimethylamine lactate.

Non-limiting examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Non-limiting examples of ethoxylated amines include PEG-cocopolyamine, PEG-15 tallow amine, quaternium-52, and the like.

Exemplary quaternary ammonium surfactants include, but are not limited to cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(coconutalkyl)dimethyl ammonium chloride, ditallowedimethyl ammonium chloride, di(hydrogenated tallow)dimethyl ammonium chloride, di(hydrogenated tallow)dimethyl ammonium acetate, ditallowedimethyl ammonium methyl sulfate, ditallow dipropyl ammonium phosphate, and ditallow dimethyl ammonium nitrate.

At low pH, amine oxides can protonate and behave similarly to N-alkyl amines. Examples include, but are not limited to, dimethyl-dodecylamine oxide, oleyldi(2-hydroxyethyl)amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

Amphoteric or zwitterionic surfactants are molecules that contain acidic and basic moieties and have the capacity of behaving either as an acid or a base. Suitable surfactants can be any of the amphoteric surfactants known or previously used in the art of surfactant compositions. Exemplary amphoteric surfactant classes include but are not limited to amino acids (e.g., N-alkyl amino acids and N-acyl amino acids), betaines, sultaines, and alkyl amphocarboxylates.

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

Examples of suitable betaines include, but are not limited to, lauryl betaine, coco betaine, oleyl betaine, cocohexadecyl dimethylbetaine, lauryl amidopropyl betaine, cocoamidopropyl betaine, and cocamidopropyl hydroxysultaine.

Exemplary alkylamphocarboxylates include, but are not limited to, sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

The nonionic surfactant can be any of the nonionic surfactants known or previously used in the art of surfactant compositions. Suitable nonionic surfactants include, but are not limited to, aliphatic ($C_6$-$C_{18}$) primary or secondary linear or branched chain acids, alcohols or phenols; alkyl ethoxylates; alkyl phenol alkoxylates (especially ethoxylates and mixed ethoxy/propoxy moieties); block alkylene oxide condensates of alkyl phenols; alkylene oxide condensates of alkanols; and ethylene oxide/propylene oxide block copolymers. Other suitable nonionic surfactants include mono- or dialkyl alkanolamides; alkyl polyglucosides (APGs); sorbitan fatty acid esters; polyoxyethylene sorbitan fatty acid esters; polyoxyethylene sorbitol esters; polyoxyethylene acids, and polyoxyethylene alcohols. Other examples of suitable nonionic surfactants include coco mono- or diethanolamide, coco glucoside, decyl diglucoside, lauryl diglucoside, coco diglucoside, polysorbate 20, 40, 60, and 80, ethoxylated linear alcohols, cetearyl alcohol, lanolin alcohol, stearic acid, glyceryl stearate, PEG-100 stearate, laureth 7, and oleth 20.

In another embodiment, non-ionic surfactants include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam™ E10, Glucam™ E20, Glucam™ P10, and Glucam™ P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate™ DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357, the disclosures of which are hereby incorporated by reference in their entirety.

Other surfactants which can be utilized are set forth in more detail in WO 99/21530, U.S. Pat. Nos. 3,929,678, 4,565,647, 5,720,964, and 5,858,948. In addition, suitable surfactants are also described in McCutcheon's Emulsifiers and Detergents (North American and International Editions, by Schwartz, Perry and Berch) which is hereby fully incorporated by reference.

While the amounts of the surfactant utilized can vary widely depending on a desired application, the amounts which are often utilized generally range from about 1% to about 80% by weight in one aspect, from about 3% to about 65% weight in another aspect, from about 5% to about 30% by weight in still another aspect, from about 6% to about 20% by weight in a further aspect, and from about 8% to about 16% by weight, based upon the total weight of the personal care, home care, health care, and institutional and industrial care composition in which it is included.

Light Screening Agents

Light screening agents are advantageously selected from UV-A, UV-B, UV-C and/or broadband filters. Examples of UV-B or broad spectrum screening agents, i.e. substances having absorption maximums between about 290 and 340 nm, may be organic or inorganic compounds. Organic UV-B or broadband screening agents are e.g. acrylates such as 2-ethylhexyl 2-cyano-3,3-diphenylacrylate (octocrylene, PARSOL™ 340), ethyl 2-cyano-3,3-diphenylacrylate and the like; camphor derivatives such as 4-methyl benzylidene camphor (PARSOL™ 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL™ MCX), ethoxyethyl methoxycinnamate, diethanolamine methoxycinnamate (PARSOL™ Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4, 2,2',4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene) propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as polysilicone-15 (PARSOL™ SLX); drometrizole trisiloxane (Mexoryl XL); imidazole derivatives such as e.g. 2-phenyl benzimidazole sulfonic acid and its salts (PARSOL™ HS). Salts of 2-phenyl benzimidazole sulfonic acid are e.g. alkali salts such as sodium- or potassium salts, ammonium salts, morpholine salts, salts of primary, sec. and tert. amines like monoethanol amine salts, diethanol amine salts and the like; salicylate derivatives such as isopropylbenzyl salicylate, benzyl salicylate, butyl salicylate, ethylhexyl salicylate (PARSOL™ EHS, NEO Heliopan OS), isooctyl salicylate or homomethyl salicylate (homosalate, PARSOL™ HMS, NEO Heliopan OS) and the like; triazine derivatives such as ethylhexyl triazone (Uvinul T-150), diethylhexyl butamido triazone (Uvasorb HEB); Encapsulated UV-filters such as encapsulated ethylhexyl methoxycinnamate (Eusolex UV-pearls) or microcapsules loaded with UV-filters as e.g. disclosed in EP 1471995 and the like. Inorganic compounds are pigments such as microparticulated $TiO_2$, ZnO and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Examples of broad spectrum or UV-A screening agents i.e. substances having absorption maximums between about 320 and 400 nm may be organic or inorganic compounds e.g. dibenzoylmethane derivatives such as 4-tertbutyl-4'-methoxydibenzoyl-methane (PARSOL™ 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3,-tetramethylbuty-1)-phenol (TINOSORB M) and the like; bis-ethylhexyloxy-phenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-Diethylamino-2-hydroxy-benzoyl) benzoic acid hexylester (Uvinul A plus) as described in the European Patent Publication EP 1046391; Ionic UV-A filters as described in the International Patent Publication WO2005080341 A1; Pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL™ 1789 stabilized by, e.g. 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

Silicone Fluids

Volatile silicone oils include cyclic and linear polydimethylsiloxanes, low molecular weight organo-functional silicones, and the like. Cyclic volatile silicones (cyclomethicones) typically contain about 3 to about 7 silicon atoms, alternating with oxygen atoms, in a cyclic ring structure. Each silicon atom is typically substituted with two alkyl groups, such as, for example, methyl groups. Volatile linear polydimethylsiloxanes (dimethicones) typically contain about 2 to about 9 silicon atoms, alternating with oxygen atoms in a linear arrangement. Each silicon atom is also substituted with two alkyl groups (the terminal silicon atoms are substituted with three alkyl groups), such as, for example, methyl groups. The linear volatile silicones typically have viscosities of less than about 5 cP at 25° C., while the cyclic volatile silicones typically have viscosities of less than about 10 cP at 25° C. "Volatile" means that the silicone has a measurable vapor pressure, or a vapor pressure of at least 2 mm of Hg at 20° C. Non-volatile silicones have a vapor pressure of less than 2 mm Hg at 20° C. A description of volatile silicones is found in Todd and Byers, Volatile Silicone Fluids for Cosmetics, Cosmetics and Toiletries, Vol. 91, pp. 29-32, 1976, and in Kasprzak, Volatile Silicones, Soap/Cosmetics/Chemical Specialties, pp. 40-43, December 1986, each incorporated herein by reference.

Exemplary volatile cyclomethicones are D4 cyclomethicone (octamethylcyclotetrasiloxane), D5 cyclomethicone (decamethylcyclopentasiloxane), D6 cyclomethicone, and blends thereof (e.g., D4/D5 and D5/D6). Volatile cyclomethicones and cyclomethicone blends are commercially available from G.E. Silicones as SF1173, SF1202, SF1256, and SF1258, Dow Corning Corporation as Dow Corning™ 244, 245, 246, 345, and 1401 Fluids. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning Corporation as Dow Corning 200™ Fluid (e.g., product designations 0.65 CST, 1 CST, 1.5 CST, and 2 CST) and Dow Corning™ 2-1184 Fluid.

Exemplary volatile low molecular weight organo-functional silicones include phenyl trimethicone, caprylyl trimethicone, caprylyl methicone, and hexyl methicone, and blends thereof. Low molecular weight organo-functional silicones are commercially available from Clariant under the trade name Silcare™ 41M10, Slicare™ 31M60, Silcare™ 41M10, and Silcare™ 41M15.

The non-volatile silicone oils useful as organic phases can be linear and typically have viscosities from about 10 cP to about 100,000 cP at 25° C. They typically contain above about 10 dialkyl/diaryl or monoalkyl/monoaryl substituted silicon atoms, alternating with oxygen atoms in a linear arrangement. They include polyalkylsiloxane, polyarylsiloxane, and polyalkylarylsiloxane polymers. Exemplary non-volatile silicone oils include the polydimethylsiloxanes (dimethicones), polydiethylsiloxanes, polymethylphenylsiloxanes, and the like. In one aspect, the non-volatile silicone oil is selected from a non-volatile polydimethylsiloxane having a viscosity range from about 10 cP to about 100,000 cP at 25° C. Non-volatile dimethicones are commercially available from Dow Corning Corporation as Dow Corning 200™ Fluid (product designations 10 CST through 10,000 CST).

Uses and Compositions

The structurant polymers can be employed in any organic phase composition, and the organic phase compositions containing said structurant polymers can be utilized in any personal care, home care, health care, and institutional and industrial care composition requiring rheology, sensory and/or aesthetic property modification. In a given composition or application, the structurant polymers or organic phase compositions containing the structurant polymer can, but need not, serve more than one function, such as a thickener, stabilizer, emulsifier, film former, deposition aid, emollient, and the like.

The personal care, home care, health care, and institutional and industrial care organic phase compositions can be packaged and dispensed from containers such as jars, tubes, sprays, wipes, roll-ons, sticks and the like, without limitation. There is no limitation as to the form of the product in which these compositions can be incorporated, so long as the purpose for which the product is used is achieved. For example, personal and health care products containing the organic phase compositions can be applied to the skin, hair, scalp, and nails, without limitation in the form of gels, sprays (liquid or foams), emulsions (creams, lotions, pastes), liquids (rinses, shampoos), bars, ointments, suppositories, and the like. The organic phase compositions can be employed, for example, in oil compositions, water-in-oil emulsions, oil-in-water emulsions, oil-in-oil emulsions, oil-in-silicon emulsions, and in silicone-in-oil emulsions.

In one personal care aspect, the organic phase compositions are suitable for preparation of personal care (cosmetics, toiletries, cosmeceuticals), including, without limitation, hair care products (shampoos, combination shampoos, such as "two-in-one" conditioning shampoos), pre-shampoo treatments and serums, post-shampoo rinses, setting and style maintenance agents (including setting aids, such as gels and sprays, grooming aids such as pomades, conditioners, perms, relaxers, hair smoothing products, hair oils and the like), skin care products (facial, body, hands, scalp and feet), such as creams, lotions, body oils, and cleansing products, antiacne products, antiaging products (exfoliant, keratolytic, anticellulite, antiwrinkle, and the like), skin protectants (sun care products, such as sunscreens, sunblock, barrier creams, oils, silicones and the like), skin color products (whiteners, lighteners, sunless tanning accelerators and the like), hair colorants (hair dyes, hair color rinses, highlighters, bleaches and the like), pigmented skin colorants (face and body makeups, foundation creams, mascara, rouge, lip products, and the like) bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softness, and the like), pharmaceutical creams, ointments, and other medicated types of skin care products.

Toiletries and beauty aids containing the organic phase compositions can include, without limitation, hair-removal products (shaving creams and lotions, epilators, after-shaving skin conditioner, and the like), hair growth promoting products, deodorants and antiperspirants, oral care products (mouth, teeth, gums), such as mouth wash, dentifrice, such as toothpaste, tooth powder, tooth polishes, tooth whiteners, breath fresheners, denture adhesives, and the like; facial and body hair bleach and the like. Other beauty aids that can contain the organic phase compositions include, without limitation, sunless tanning applications containing artificial tanning accelerators, such as dihydroxyacetone (DHA), tyrosine, tyrosine esters and the like: skin depigmenting, whitening and lightening, formulations containing such active ingredients as kojic acid, hydroquinone, arbutin, fruital, vegetable or plant extracts, (lemon peel extract, chamomile, green tea, paper mulberry extract, and the like), ascorbyl acid derivatives ascorbyl palmitate, ascorbyl stearate, magnesium ascorbyl phosphate and the like).

The organic phase compositions can be suitable for dermal cleansing products containing particulates, insoluble benefit agents, microabrasives, and abrasives and combinations thereof. Dermal cleansing products include shampoos, body washes, shower gels, bath gels, masks and skin cleansers.

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by mixing the components described above.

The invention herein is useful for thickening an oil composition, improving clarity of the oil composition, or both, which may be better understood with reference to the following examples.

EXAMPLES

In the following examples, viscosity was measured on a TA Instrument rheometer (AR 1000, AR 2000, or HR-2) in flow mode using a 4 cm stainless steel 2° cone and measuring at 20° C. Shear rates were captured from 1 to 1000 s$^{-1}$ but reported only at 1 s$^{-1}$.

Moduli (G' and G") are shown to highlight the samples that are gels vs. liquids and values are obtained from a stress sweep (at 0.01% strain) of the sample using the same TA Instrument rheometer. Reported values were at a stress of approximately 0.01 Pa. Clarity is reported as either a visual observation, or as an average transmission as measured on a Brinkman PC950 colorimeter.

Example 1

Sample Polymer 1 ("SP1")—To a 500 ml reaction kettle outfitted with an overhead stirrer and a nitrogen port and a Dean Stark trap, 200 ml of toluene, 0.01207 moles of 1-hexadecanol, 0.03614 moles of a hydrogenated polybutadiene having a number average molecular weight ("Mn") of about 1500 (Nisso PB™ GI-1000) were added with stirring (350 rpm) and the solution was heated to reflux to remove any residual water through the toluene-water azeotrope. After water removal, the solution was cooled to 70° C. and 0.04219 moles of hexamethylene diisocyanate was added and stirred for 10 min. Three drops (~30 microliters) of a bismuth carboxylate catalyst (K-Kat™ 348 from King Industries) was added and an exotherm was immediately noticed. The reaction was allowed to run for 2 hours or until all of the isocyanate was reacted (by FTIR; peak at 2270 cm-1). After solvent removal in vacuum, the structurant polymer was collected. Mn=14K; polydispersity ("PDI")=2.4.

The $\Delta HSP_{o\text{-}p}$ between SP1 and sunflower oil or mineral oil was calculated using the Y-MB method as described in "Hansen Solubility Parameters: A User's Handbook", C. M. Hansen, CRC Press: Boca Raton, Fla., 2007. The $\Delta HSP_{o\text{-}p}$ for the sunflower oil mixture was 3.6 $(J/cm^3)^{1/2}$, which gave a visually clear composition. The $\Delta HSP_{o\text{-}p}$ of the mineral oil mixture was about 4.7 $(J/cm^3)^{1/2}$, which gave a hazy composition.

SP1 was further tested for its thickening efficiency by heating the structurant polymer in sunflower oil between 70-90° C. for 24 hours, cooling the mixture and allowing the mixture to equilibrate over a period of several days to a week. The viscosity (at 1 sec$^{-1}$) of the mixture was found to be proportional to the concentration of the thickener as shown in Table 1 below.

TABLE 1

| Wt. % SP1 | Viscosity (Pa · s @ 1 s$^{-1}$) |
|---|---|
| 0 | 0 |
| .5 | 0.2 |
| 1.2 | 0.75 |
| 2.5 | 2.75 |
| 4.0 | 6.25 |
| 4.5 | 9.8 |
| 5 | 11.92 |

At 5 wt. % loading, SP1 improved the viscosity of various different oils as shown in Table 2 below.

TABLE 2

| Organic phase | Viscosity with No Structurant Polymer (Pa · s @ 1 s$^{-1}$) | Viscosity with 5 wt. % SP1 (Pa · s @ 1 s$^{-1}$) |
|---|---|---|
| Capric/Caprylic Triglyceride | 0.03 | 3.04 |
| Sunflower Oil | 0.06 | 11.92 |
| Cetearyl Ehtylhexanoate | 0.01 | 0.95 |
| Octyl/Ethylhexyl Stearate | 0.02 | 2.53 |
| Dioctyl Ether | 0.002 | 1.72 |
| Mineral Oil | 0.02 | 18.04 |
| Isohexadecane | 0.004 | 11.66 |
| Isododecane | 0.004 | 10.27 |
| Jojoba Oil | 0.05 | 9.22 |
| Safflower Oil | 0.05 | 13.44 |
| $C_{12\text{-}15}$ alkyl benzoate | 0.01 | 2.13 |

The rheology of SP1 at 5 wt. % was found to be thixotropic with a recovery time of from minutes to days, depending on the polarity of the oil.

Stoichiometric variants of SP1 were prepared changing the level of 1-hexadecanol to alter the Mn of the resultant structurant polymer. Table 3 below shows the resulting structurant polymers SP2 to SP5 and the corresponding molecular weights with clarity at 5 wt. % in sunflower oil.

TABLE 3

| Sample | Actual Mn | Actual Mw | PDI | Relative Clarity* |
|---|---|---|---|---|
| SP2 | 6,293 | 10,535 | 1.674 | 0.18 |
| SP3 | 13,992 | 33,694 | 2.408 | 0.93 |
| SP4 | 18,262 | 53,967 | 2.955 | 1.00 |
| SP5 | 21,051 | 70,139 | 3.332 | 0.90 |

*Measured employing a Brinkman PC950 colorimeter (highest clarity = 1.00)

The influence of molecular weight and polydispersity on rheology was also tested by blending the various structurant polymers into sunflower oil. The results are shown in Table 4 below.

TABLE 4

| Blend Sample | Structurant Polymer | | | | Calculated Mn | Relative Clarity | Storage Modulus G' (Pa) | Loss Modulus G" (Pa) |
|---|---|---|---|---|---|---|---|---|
| | SP2 | SP3 | SP4 | SP5 | | | | |
| 1 | 1 | | | | 6,293 | 0.18 | 0.1 | 1.2 |
| 2 | | 1 | | | 13,992 | 0.93 | 27.2 | 18.4 |
| 3 | | | 1 | | 18,262 | 1.00 | 1.2 | 3.6 |
| 4 | | | | 1 | 21,051 | 0.90 | 0.9 | 3.3 |
| 5 | 1 | 1 | 1 | 1 | 14,900 | 0.74 | 17.7 | 8.3 |
| 6 | 1 | | | 1 | 13,672 | 0.25 | 4.7 | 4.5 |
| 7 | 1 | 1 | | | 10,143 | 0.20 | 5.3 | 4.8 |
| 8 | | | 1 | | 12,278 | 0.15 | 6.4 | 5.1 |
| 9 | 1 | | | 1 | 13,672 | 0.28 | 5.8 | 4.8 |
| 10 | | 1 | | 1 | 17,522 | 0.90 | 2.5 | 5.2 |

Example 2

Comparative Sample Polymer 1 ("CSP1")—To a 500 ml reaction kettle outfitted with an overhead stirrer and a nitrogen port and a Dean Stark trap, 200 ml of toluene, 0.0121 moles of 1-hexadecanol, 0.0361 moles of a hydrogenated polybutadiene having an Mn of about 2,100 (Nisso PB™ GI-2000) were added with stirring (350 rpm) and the solution was heated to reflux to remove any residual water through the toluene-water azeotrope. After water removal, the solution was cooled to 70° C. and 0.0.0422 moles of hexamethylene diisocyanate was added and stirred for 10 min. Three drops (~30 microliters) of a bismuth carboxylate catalyst (K-Kat™ 348 from King Industries) is added and an exotherm was immediately noticed. The reaction was allowed to run for 2 hours until all of the isocyanate was reacted (by FTIR; peak at 2,270 cm$^{-1}$). After solvent removal in vacuum, the polymer was collected. Mn=17K; PDI=6.5.

The $\Delta HSP_{o\text{-}p}$ between CSP1 and sunflower oil or mineral oil was calculated using the Y-MB method as described in "Hansen Solubility Parameters: A User's Handbook", C. M. Hansen, CRC Press: Boca Raton, Fla., 2007. The $\Delta HSP_{o\text{-}p}$ for the sunflower oil mixture was 1.9 $(J/cm^3)^{1/2}$, which gave a clear composition. The $\Delta HSP_{o\text{-}p}$ of the mineral oil mixture was about 3.5 $(J/cm^3)^{1/2}$, which gave a clear but slightly hazy composition.

CSP1 was further tested for its thickening efficiency by heating the structurant polymer in sunflower oil between 70-90° C. for 24 hours, cooling the mixture and allowing the mixture to equilibrate over a period of several days to a week. The viscosity (at 1 sec$^{-1}$) of the mixture was found to be unchanged from baseline.

Example 3

Sample Polymer 6—The procedure for preparing CSP1 was followed except that 0.0361 moles of the hydrogenated polybutadiene was added and the polymerization reaction was allowed to run for 1 hour before 0.0121 moles of 1-hexadecylamine was added. After addition of the chain extender, the reaction was allowed to run for 1 additional hour until all of the isocyanate was reacted (by FTIR; peak at 2,270 cm-1). After solvent removal in vacuum, the polymer was collected. Mn=19K; PDI=3.5.

The $\Delta HSP_{o-p}$ between SP6 and sunflower oil or mineral oil was calculated using the Y-MB method as described in "Hansen Solubility Parameters: A User's Handbook", C. M. Hansen, CRC Press: Boca Raton, Fla., 2007. The $\Delta HSP_{o-p}$ for the sunflower oil mixture was 2.01 $(J/cm^3)^{1/2}$, which gave a clear composition. The $\Delta HSP_{o-p}$ of the mineral oil mixture was about 3.8 $(J/cm^3)^{1/2}$, which gave a clear but slightly hazy composition.

SP6 was further tested for its thickening efficiency by heating the structurant polymer in sunflower oil between 70-90° C. for 24 hours, cooling the mixture and allowing the mixture to equilibrate over a period of one week before measuring viscosity. The viscosity (at 1 $sec^{-1}$) of the mixture was found to thicken the sunflower oil to 1 Pa·s from around 0.06 Pa·s at 20° C. (as shown in table 2).

Example 4

Sample Polymer 7—To a 500 ml reaction kettle outfitted with an overhead stirrer and a nitrogen port and a Dean Stark trap, 200 ml of toluene, 0.0036 moles of a hydrogenated polybutadiene having an Mn of about 2,100 (Nisso PB™ GI-2000) and 0.0325 moles of a dimer diol (Pripol™ 2030*) were added with stirring (350 rpm) and the solution was heated to reflux to remove any residual water through the toluene-water azeotrope. After water removal, the solution was cooled to 70° C. and 0.0422 moles of hexamethylene diisocyanate was added and stirred for 10 min. Three drops (~30 microliters) of a bismuth carboxylate catalyst (K-Kat™ 348 from King Industries) was added and an exotherm was immediately noticed. The reaction was allowed to run for 1 hour before 0.0.0121 moles of a 1-octadecylalcohol was added, and the reaction was allowed to continue for an additional 1 hour until all of the isocyanate was reacted (by FTIR; peak at 2,270 cm-1). After solvent removal in vacuum, the polymer was collected. Mn=25K; PDI=2.3.

*a dimer having an average hydroxy group number of between 204-212 with a structure of a roughly C36 diol coupled at the 9,10 position The solid polymer (5 wt %) is added to sunflower oil and heated to 75° C. until all of the solid was homogeneously mixed into solution which was highly translucent but not clear. Upon cooling, the solution gelled and became more turbid. The viscosity (at 1 $sec^{-1}$) of the mixture was found to be proportional to the concentration of the thickener as shown in Table 5 below.

TABLE 5

| Wt. % SP7 | Viscosity (Pa · s @ 1 $s^{-1}$) |
|---|---|
| 0 | 0.06 |
| 0.75 | 1 |
| 1.25 | 10 |
| 2.5 | 45 |
| 5 | 233 |

Example 5

Sample Polymer 8—To a 500 ml reaction kettle outfitted with an overhead stirrer and a nitrogen port was added 0.1054 mole of dimer diol (Pripol 2030*) and 0.105 mole of ε-caprolactone (Sigma Aldrich) and mixed thoroughly at 300 rpm with a Teflon paddle stirring blade. 30 ppm of a bismuth carboxylate catalyst (K-Kat™ 348 from King Industries) was then added and the entire solution was heated to 125° C. The reaction of the caprolactone with the dimer diol was followed by FTIR (carbonyl band shifts from 1,725 cm-1 to 1,735 cm-1). The reaction was allowed to continue until all of the caprolactone was consumed to give a low viscosity water white liquid. At this point the solution was cooled to room temperature and 0.0130 mole of a hydrogenated polybutadiene having an Mn of about 2100 (Nisso PB™ GI-2000) in 200 ml of toluene was added with constant stirring followed by 0.143 moles of hexamethylene diisocyanate. The reaction mixture was heated to 70° C. and the consumption of isocyanate was monitored (by FTIR; peak at 2,270 cm-1). The reaction was allowed to run for 1 hour (isocyanate concentration reached a minimum) and then 0.0484 moles of 1-octadecylalcohol was added and the reaction was allowed to run for 1 additional hour until all of the isocyanate was reacted (by FTIR; peak at 2,270 cm-1). After solvent removal in vacuum, the polymer was collected. Mn=24,000; PDI=2.2.

*a dimer having an average hydroxy group number of between 204-212 with a structure of a roughly C36 diol coupled at the 9,10 position 5 wt. % of SP8 was dissolved in caprylic capric triglyceride at 75° C. and cooled to room temperature to produce a translucent viscous gel viscosity of 1.7 Pa·s at (1 $sec^{-1}$ and 20° C.).

Example 6

Sample Polymer 9—To a 500 ml reaction kettle outfitted with an overhead stirrer and a nitrogen port and 200 ml of toluene, 0.0067 moles of a hydrogenated polybutadiene having an Mn of about 3300 (Cray Valley HLBH-3000) and 0.0325 moles of a dimer diol (Pripol™ 2030) were added with stirring (350 rpm) and heated to 70° C. Then, 0.0422 moles of hexamethylene diisocyanate was added and stirred for 10 min. Three drops (~30 microliters) of a bismuth carboxylate catalyst (K-Kat™ 348 from King Industries) was added and an exotherm was immediately noticed. The reaction was allowed to run for 1 hour before 0.0079 moles of a 1-octadecylalcohol was added, and the reaction was allowed to continue for an additional 1 hour until all of the isocyanate was reacted (by FTIR; peak at 2,270 cm-1). After solvent removal in vacuum, the polymer was collected. Mn=25,000; PDI=2.8. This polymer showed similar thickening efficiency at 1 wt % as Sample Polymer 7 but increased clarity in all oils.

Example 7

Sample Polymer 10—To a 500 ml reaction kettle outfitted with an overhead stirrer and a nitrogen port and 200 ml of toluene, 0.00586 moles of a hydrogenated polybutadiene having an Mn of about 3800 (Nisso GI-3000) and 0.0234 moles of a dimer diol (Pripol™ 2030) were added with stirring (350 rpm) and heated to 70° C. Then, 0.0322 moles of hexamethylene diisocyanate was added and stirred for 10 min. Three drops (~30 microliters) of a bismuth carboxylate catalyst (K-Kat™ 348 from King Industries) was added and an exotherm was immediately noticed. The reaction was allowed to run for 1 hour before 0.00585 moles of monohydroxyl-hydrogenated polybutadiene (Cray Valley HLBH-5000M; MW 5000) was added, and the reaction was allowed to continue for an additional 1 hour until all of the isocyanate was reacted (by FTIR; peak at 2,270 cm-1). After solvent removal in vacuum, the polymer was collected. Mn=20K; PDI=3.1. Material when added at 1 wt % to sunflower oil showed a viscosity of 1.1 Pa·s (at 20 $sec^{-1}$) and no decrease in clarity.

Example 8

Sample Polymer 11—To a 500 ml reaction kettle outfitted with an overhead stirrer and a nitrogen port was added 0.133 mole of dimer diol (Pripol 2030) and 0.1 mole of dimer acid (Pripol 1006) and mixed thoroughly at 300 rpm with a Teflon paddle stirring blade. 30 ppm of a bismuth carboxylate catalyst (K-Kat™ 348 from King Industries) was then added and the entire solution was heated to 125° C. The reaction of the dimer acid with the dimer diol was followed by FTIR (carbonyl band shifts from ~1,700 cm-1 to 1,735 cm-1). The reaction was allowed to continue until all of the dimer acid was consumed to give a low viscosity water white liquid. The Mn of the resulting diol was 3150; PDI=2.4. To a 500 ml reaction kettle outfitted with an overhead stirrer and a nitrogen port and a Dean Stark trap, 200 ml of toluene, 0.0067 moles of the reaction product diol above and 0.0325 moles of a dimer diol (Pripol™ 2030) were added with stirring (350 rpm) and the solution was heated to reflux to remove any residual water through the toluene-water azeotrope. After water removal, the solution was cooled to 70° C. and 0.0422 moles of hexamethylene diisocyanate was added and stirred for 10 min. Three drops (~30 microliters) of a bismuth carboxylate catalyst (K-Kat™ 348 from King Industries) was added and an exotherm was immediately noticed. The reaction was allowed to run for 1 hour before 0.0079 moles of a 1-octadecylalcohol was added, and the reaction was allowed to continue for an additional 1 hour until all of the isocyanate was reacted (by FTIR; peak at 2,270 cm-1). After solvent removal in vacuum, the polymer was collected. Mn=11.3K; PDI=2.7. Addition of 1 wt % of this polymer to sunflower oil resulted in a hazy, but translucent gelled fluid with a viscosity of 1.2 Pa·s (at 20 sec$^{-1}$)

Example 9

Sample polymer 12—To a 500 ml reaction kettle outfitted with an overhead stirrer and a nitrogen port and 200 ml of toluene, 0.0115 moles of a hydrogenated polybutadiene having an Mn of about 3300 (Cray Valley HLBH-3000) and 0.0413 moles of a dimer diol (Pripol™ 2030) and 0.0011 moles of polydimethylsiloxane, hydroxyl terminated (Sigma Aldrich ~750 cSt; MW ~950) were added with stirring (350 rpm) and heated to 70° C. Then, 0.0593 moles of hexamethylene diisocyanate was added and stirred for 10 min. Three drops (~30 microliters) of a bismuth carboxylate catalyst (K-Kat™ 348 from King Industries) was added and an exotherm was immediately noticed. The reaction was allowed to run for 1 hour before 0.0108 moles of a 1-octadecylalcohol was added, and the reaction was allowed to continue for an additional 1 hour until all of the isocyanate was reacted (by FTIR; peak at 2,270 cm-1). After solvent removal in vacuum, the polymer was collected. Mn=25K; PDI=2.8. Material when added at 1 wt % to sunflower oil showed a viscosity of 1.2 Pa·s (at 20 sec$^{-1}$) and no decrease in clarity.

Example 10

Sample polymer 13—To a 500 ml reaction kettle outfitted with an overhead stirrer and a nitrogen port and 200 ml of toluene, 0.0117 moles of a hydrogenated polybutadiene having an Mn of about 3300 (Cray Valley HLBH-3000) and 0.0413 moles of a dimer diol (Pripol™ 2030) were added with stirring (350 rpm) and heated to 70° C. Then, 0.05744 moles of hexamethylene diisocyanate was added and stirred for 10 min. Three drops (~30 microliters) of a bismuth carboxylate catalyst (K-Kat™ 348 from King Industries) was added and an exotherm was immediately noticed. The reaction was allowed to run for 1 hour before 0.0002 moles of polydimethylsiloxane, monohydroxy terminated (Sigma Aldrich; Mn 4670) was added and an additional hour before 0.0108 moles of a 1-octadecylalcohol was added, and the reaction was allowed to continue for an additional 1 hour until all of the isocyanate was reacted (by FTIR; peak at 2,270 cm-1). After solvent removal in vacuum, the polymer was collected. Mn=25K; PDI=2.8. Material when added at 1 wt % to sunflower oil showed a viscosity of 0.6 Pa·s and no decrease in clarity but a significant decrease in surface tension (from ~30 dyne/cm to ~20 dyne/cm).

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

What is claimed is:
1. An organic phase composition comprising
  A) from 0.01 to about 10 wt. % of a structurant polymer having a backbone comprised of:
     i) hard segments derived from:
        1. at least one linear non-branched aliphatic diisocyanate, or
        2. at least one linear non-branched aliphatic diisocyanate in combination with at least one chain extending compound, and
     ii) soft segments having a number average molecular weight of between about 750 and 4500 derived from
        1. at least one hydrophobic oligomer chosen from at least one of a polybutadiene, polytetrahydrofuran (pTHF), polypropylene glycol (PPG), polyester, polycaprolactone, polycarbonate, polycastor oil, fatty acid/alcohol adduct, or mixtures thereof, and

B) an organic phase,
wherein the average number average molecular weight between respective diisocyanates on the structural polymer backbone is from between about 750 to about 2,000, and the ratio of the total hydrogen bonding donor sites to the total hydrogen bonding acceptor sites in the organic phase composition is 1 or greater
wherein the ΔHSP between the organic phase and the oligomer is less than about 4.

2. The composition of claim 1, wherein the at least one hydrophobic oligomer is at least one polyol compound, polyamine compound, or mixtures thereof.

3. The composition of claim 1, wherein the oligomer is in the form of an adduct with a lactone, diacid, or mixture thereof.

4. The composition of claim 1 wherein the oligomer is modified with an alcohol, amine, anhydride, or mixture thereof.

5. The composition of claim 4, wherein the oligomer is modified with no more than 2 mole % of a diamine.

6. The composition of claim 1 wherein the structurant polymer is a polyurethane.

7. The composition of claim 1 wherein the structurant polymer is a polyurea.

8. The composition of claim 1 wherein the structurant polymer is a mixed polyurethane/polyurea.

9. The composition of claim 1, wherein the organic phase is derived from an animal oil, vegetable oil, mineral oil, synthetic oil, or mixture thereof.

10. The composition of claim 1, wherein the organic phase is hydrogenated.

11. A method of thickening an organic phase comprising adding to the organic phase up to about 10 wt. % of a structurant polymer comprising:
  i) hard segments derived from:
    1. at least one linear non-branched aliphatic diisocyanate, or
    2. at least one linear non-branched aliphatic diisocyanate in combination with at least one chain extending compound, and
  ii) soft segments having a number average molecular weight of from about 750 to about 4500 derived from
    1. at least one hydrophobic oligomer chosen from at least one of a polybutadiene, polytetrahydrofuran (pTHF), polypropylene glycol (PPG), polyester, polycaprolactone, polycarbonate, polycastor oil, fatty acid/alcohol adduct, or mixtures thereof, and
  wherein the number average molecular weight between the at least one linear non-branched aliphatic diisocyanate is from about 750 to about 2,000, and the ratio of the total hydrogen bonding donor sites to the total hydrogen bonding acceptor sites in the organic phase composition is 1 or greater
  wherein the ΔHSP between the organic phase and the oligomer is less than about 4.

* * * * *